United States Patent
Astier et al.

(10) Patent No.: US 12,030,053 B1
(45) Date of Patent: *Jul. 9, 2024

(54) MULTI-STEP KINETIC IMMUNOASSAY SYSTEMS AND METHODS

(71) Applicant: Panazee Inc., Oakland, CA (US)

(72) Inventors: Yann Astier, Oakland, CA (US); Juraj Topolancik, Redwood City, CA (US)

(73) Assignee: Panazee Inc., Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/313,183

(22) Filed: May 5, 2023

(51) Int. Cl.
  *B01L 3/00* (2006.01)
  *G01N 33/533* (2006.01)

(52) U.S. Cl.
  CPC ...... *B01L 3/502761* (2013.01); *G01N 33/533* (2013.01); *B01L 2300/0636* (2013.01)

(58) Field of Classification Search
  None
  See application file for complete search history.

(56) References Cited

U.S. PATENT DOCUMENTS

| | | |
|---|---|---|
| 7,150,812 B2 | 12/2006 | Huang et al. |
| 9,267,943 B2 | 2/2016 | Davis et al. |
| 9,919,311 B2 | 3/2018 | Puntambekar et al. |
| 10,071,359 B2 | 9/2018 | Kung et al. |
| 10,253,350 B2 | 4/2019 | Gifford et al. |
| 10,324,011 B2 | 6/2019 | D'silva et al. |
| 10,545,161 B2 | 1/2020 | Khattak et al. |
| 10,722,887 B2 | 7/2020 | Azpiroz et al. |
| 10,960,394 B2 | 3/2021 | Wu et al. |
| 11,802,870 B1 | 10/2023 | Astier et al. |
| 2009/0148436 A1 | 6/2009 | Lavallie et al. |
| 2016/0139012 A1 | 5/2016 | D'Silva et al. |

(Continued)

FOREIGN PATENT DOCUMENTS

| | | |
|---|---|---|
| WO | 9810267 A1 | 3/1998 |
| WO | 2015139022 A1 | 9/2015 |

(Continued)

OTHER PUBLICATIONS

Yasukawa, T. et al. Flow sandwich-type immunoassay in microfluidic devices based on negative dielectrophoresis, Biosensors and Bioelectronics 22 (2007) 2730-2736 (Year: 2007).*

(Continued)

*Primary Examiner* — Xiaoyun R Xu
(74) *Attorney, Agent, or Firm* — Kilpatrick Townsend & Stockton LLP

(57) ABSTRACT

A microfluidic chip with an array of pillars for directing flow of beads is used to measure reaction kinetics. A stream may be continuously drawn from the reaction volume into the microfluidic chip. The bead is attached to a primary antibody. The reaction volume has an antigen. The primary antibody binds to the antigen. A secondary antibody with a label binds to the antigen, creating a sandwich of bead, antigen, and label. The binding reactions occur over time in the microfluidic chip. The beads may be imaged after traversing a laminar wash buffer, and the signal intensity is measured. Each bead provides a kinetic monitoring of the immunoassay over the reaction time at which the bead is removed from the reaction media. Methods and systems are described in this disclosure.

24 Claims, 25 Drawing Sheets

(56) References Cited

U.S. PATENT DOCUMENTS

| | | |
|---|---|---|
| 2017/0097340 A1 | 4/2017 | Ho et al. |
| 2019/0056302 A1 | 2/2019 | Berezin et al. |
| 2019/0079083 A1 | 3/2019 | Harwanegg et al. |
| 2019/0126278 A1 | 5/2019 | Arai |
| 2020/0340910 A1 | 10/2020 | Handique |
| 2021/0198754 A1 | 7/2021 | Fan et al. |

FOREIGN PATENT DOCUMENTS

| | | |
|---|---|---|
| WO | 2021144396 A1 | 7/2021 |
| WO | 2021245635 A1 | 12/2021 |
| WO | 2022119945 A1 | 6/2022 |

OTHER PUBLICATIONS

U.S. Appl. No. 18/079,986, Non-Final Office Action, dated May 10, 2023, 18 pages.
Galvez et al., "Microfluidic Chip With Pillar Arrays for Controlled Production and Observation of Lipid Membrane Nanotubes", Lab Chip, vol. 20, Jun. 29, 2020, pp. 2748-2755.
Zakeri et al., "Peptide Tag Forming a Rapid Covalent Bond to a Protein, Through Engineering a Bacterial Adhesin", Proceedings of the National Academy of Sciences of the United States of America, vol. 109, No. 12, Mar. 20, 2012, pp. E690-E697.
Application No PCT/US2023/083898, International Search Report and Written Opinion, Mailed on May 10, 2024, 18 pages.

\* cited by examiner $$I_{\mu S}(t) \cong \frac{2I_{QD}}{[\mu S]} \times \frac{[L][A]}{[L] + [A] + K_D + \sqrt{([L] + [A] + K_D)^2 - 4[L][A]} \times coth(t/\tau)}$$

$$\text{where } 1/\tau \equiv \frac{k_{on}}{2}\sqrt{([L] + [A] + K_D)^2 - 4[L][A]}$$

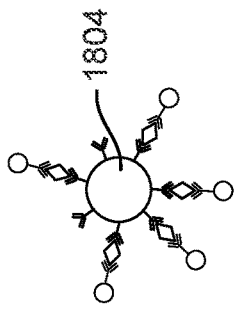

$$f_{bl}(t,[L]) \cong \frac{[L]}{[L]+\frac{\hat{K}_D}{[A_2]}} \times \left[1 - e^{-(\hat{k}_{on}[A_2][L] + k_{off}) \times t}\right] \quad 1808$$

$$f_{bl}(t,[L]) \cong \frac{[L]}{[A_1]+\frac{\hat{K}_D}{[A_2]}} \times \left[1 - e^{-(\hat{k}_{on}[A_2][A_1] + \hat{k}_{off}) \times t}\right] \cong \frac{[L]}{[A_1]} \times \left[1 - e^{-(\hat{k}_{on}[A_2][A_1] + k_{off}) \times t}\right] \quad 1812$$

$$f_{bl}(t,[L]) \cong \frac{[A_1]+[L]+\frac{\hat{K}_D}{[A_2]} + \sqrt{\left([A_1]+[L]+\frac{\hat{K}_D}{[A_2]}\right)^2 - 4[A_1][L]} \times \coth\left(t \times \frac{[A_2]\hat{k}_{on}}{2}\sqrt{\left([A_1]+[L]+\frac{\hat{K}_D}{[A_2]}\right)^2 - 4[A_1][L]}\right)}{2[L]} \quad 1816$$

Where $[X] = \frac{N_X}{\nu N_{Avog}}$, $\nu$ is the sample volume, $N_{Avog}$ is Avogadro Number ($N_{Avog} \cong 6.02214076 \times 10^{23}\ mol^{-1}$)

$\hat{k}_{on} = r_{on}(\nu N_{Avog})^2 [M^{-2} s^{-1}]$, $k_{off} = r_{off}[s^{-1}]$, and $\hat{K}_D \equiv \frac{k_{off}}{\hat{k}_{on}} = \frac{1}{(\nu N_{Avog})^2} \times \left(\frac{r_{off}}{r_{on}}\right) [M^2]$ is the dissociation constant  1820

FIG. 18

MULTI-STEP KINETIC IMMUNOASSAY SYSTEMS AND METHODS

CROSS-REFERENCE TO RELATED APPLICATION

This application relates to U.S. Non-Provisional patent application Ser. No. 18/079,986, filed Dec. 13, 2022, entitled "KINETIC IMMUNOASSAY SYSTEMS AND METHODS," the entire contents of which are incorporated herein by reference.

BACKGROUND

Typical immunoassay technology carries out antibody binding reactions reported by a label. The label measurement indicates the number of bound complexes after a combination of binding steps and wash procedures. The wash procedures aim to remove excess label to avoid misrepresentation of the reaction label measurement.

FIG. 1 shows an example of a typical immunoassay. At stage 104, antibodies (e.g., antibody 108) are attached to a surface. Antigens (e.g., antigen 112) are in solution and may be captured by an antibody. The surface is washed to remove unbound antigens.

At stage 116, a labeling antibody (e.g., antibody 120 with label 124) is introduced. Labeling antibodies bind to antigens that are bound to antibodies that are attached to the surface. The surface is washed again to remove unbound labeling antibodies.

At stage 128, a signal from the label is measured. A quantity of labels is determined from the signal. A quantity of antigens is determined from the signal.

Immunoassay technologies currently available interrupt the binding reaction to prepare the sample for label read out. The measurement is only representative of the number of molecules having reacted up to the point when the reaction was interrupted. To repeat measurements for a specific reaction time, the incubation time of the reaction and each wash procedure should be identical, which requires a rigorous procedure. Calibration reactions may also need to be carried out simultaneously to benchmark the label measurement.

Interrupting the binding reaction to fix the label intensity for read out results in an immunoassay measurement of a single point in time. Unless the reaction is incubated for several hours to reach reaction equilibrium, the point at which the reaction is interrupted takes place during a non-equilibrium binding kinetic phase of the reaction. The single point measurement is impacted by the quality of the mixing, washing procedures, temperature, and other factors and can show great variability.

Embodiments described herein allow for real-time measurement of binding reactions accurately and efficiently. Embodiments include these and other improvements.

BRIEF SUMMARY

A microfluidic chip with an array of pillars for directing flow of beads is used to measure reaction kinetics. A nano/microliter stream may be continuously drawn from the reaction volume into the microfluidic chip. The bead may be attached to a primary antibody. The reaction volume may have an antigen. The primary antibody may bind to the antigen in the reaction volume. A secondary antibody with a fluorescent label may bind to the antigen, creating a sandwich of bead, antigen, and label either in the reaction volume or along an output path from the reaction volume.

A washing buffer removes non-specific interactions (unbound labels and antigens) from the bead surface after the beads are extracted from the reaction volume. The beads may be imaged after traversing a laminar wash buffer, and the signal intensity is measured. The beads may be drawn from the binding reaction continuously over the duration of the reaction. When the beads arrive at the point of imaging and/or signal measurement, each bead has the same "time of flight" from leaving the reaction media through wash, and imaging. This means that each bead measurement represents the progress of the immunoassay at the time of the specific bead leaving the reaction volume. Each bead provides a kinetic monitoring of the immunoassay over the reaction time at which the bead is removed from the reaction media. The microfluidic chip can be used to detect low concentrations of a target analyte.

In embodiments, methods may include mixing a first plurality of beads with a sample to form a first mixture in a reactor of a microfluidic chip. The sample may include a plurality of analytes. Each bead of the first plurality of beads may be coupled to an affinity reagent. The affinity reagent may be configured to bind to the analyte. Methods may in addition include binding a first subset of the plurality of analytes to a plurality of affinity reagents coupled to the first plurality of beads in the reactor. Methods may further include flowing a first portion of the first mixture from the reactor through a first fluidic path defined by a plurality of structures in the microfluidic chip. The first portion of the first mixture may include the first plurality of beads coupled to a first subset of the plurality of affinity agents. Methods may further include coupling the first plurality of beads to a plurality of label compounds in the first fluidic path. Methods may in addition include forming a second mixture by flowing a solution in a second fluidic path. The second fluidic path intersects the first fluidic path. Methods may also include measuring an amount of the plurality of label compounds in the second mixture. Other embodiments of this aspect include corresponding computer systems, apparatus, and computer programs recorded on one or more computer storage devices, each configured to perform the actions of the methods.

In embodiments, methods may include mixing a first plurality of beads with a sample to form a mixture in a reactor of a microfluidic chip. The sample may include a plurality of analytes and a plurality of labels. Each bead of the first plurality of beads may be coupled to an affinity reagent. The affinity reagent may be configured to bind to the analyte. The plurality of labels may be configured to bind to the analyte. Methods may in addition include binding the plurality of analytes to a plurality of affinity agents coupled to the first plurality of beads. Methods may also include coupling a first subset of the plurality of labels to the first plurality of beads in the reactor. Methods may further include flowing a first portion of the mixture from the reactor through a first fluidic path defined by a plurality of structures in the microfluidic chip. The first portion of the mixture may include the first plurality of beads coupled to the first subset of the plurality of labels. Methods may in addition include forming a second mixture by flowing a solution in a second fluidic path. The second fluidic path may intersect the first fluidic path. Methods may also include measuring an amount of the first subset of the plurality of labels in the second mixture. Other embodiments may include corresponding computer systems, apparatus, and computer programs recorded on one or more computer storage devices, each configured to perform the actions of the methods.

In embodiments, systems may include a microfluidic chip. The microfluidic chip may include a reactor. The microfluidic chip may further include a plurality of structures defining a first fluidic path. The first fluidic path may be in fluid communication with the reactor, a reactant reservoir, a solution reservoir, and a manifold. The manifold may be configured to deliver a reactant from the reactant reservoir to intersect the first fluidic path. The manifold may also be configured to deliver a solution from the solution reservoir to intersect the first fluidic path. Systems may in addition include a plurality of beads disposed on the microfluidic chip. Each bead of the plurality of beads may have a diameter smaller than a width of the first fluidic path. Each bead of the plurality of beads may be bound to a first affinity reagent. Systems may also include an imaging detector.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A better understanding of the nature and advantages of embodiments of the present invention may be gained with reference to the following detailed description and the accompanying drawings.

BRIEF DESCRIPTION OF THE DRAWINGS

FIG. 18 shows approximate solutions for experimentally relevant limiting cases according to embodiments of the present invention.

DETAILED DESCRIPTION

Figure 1:
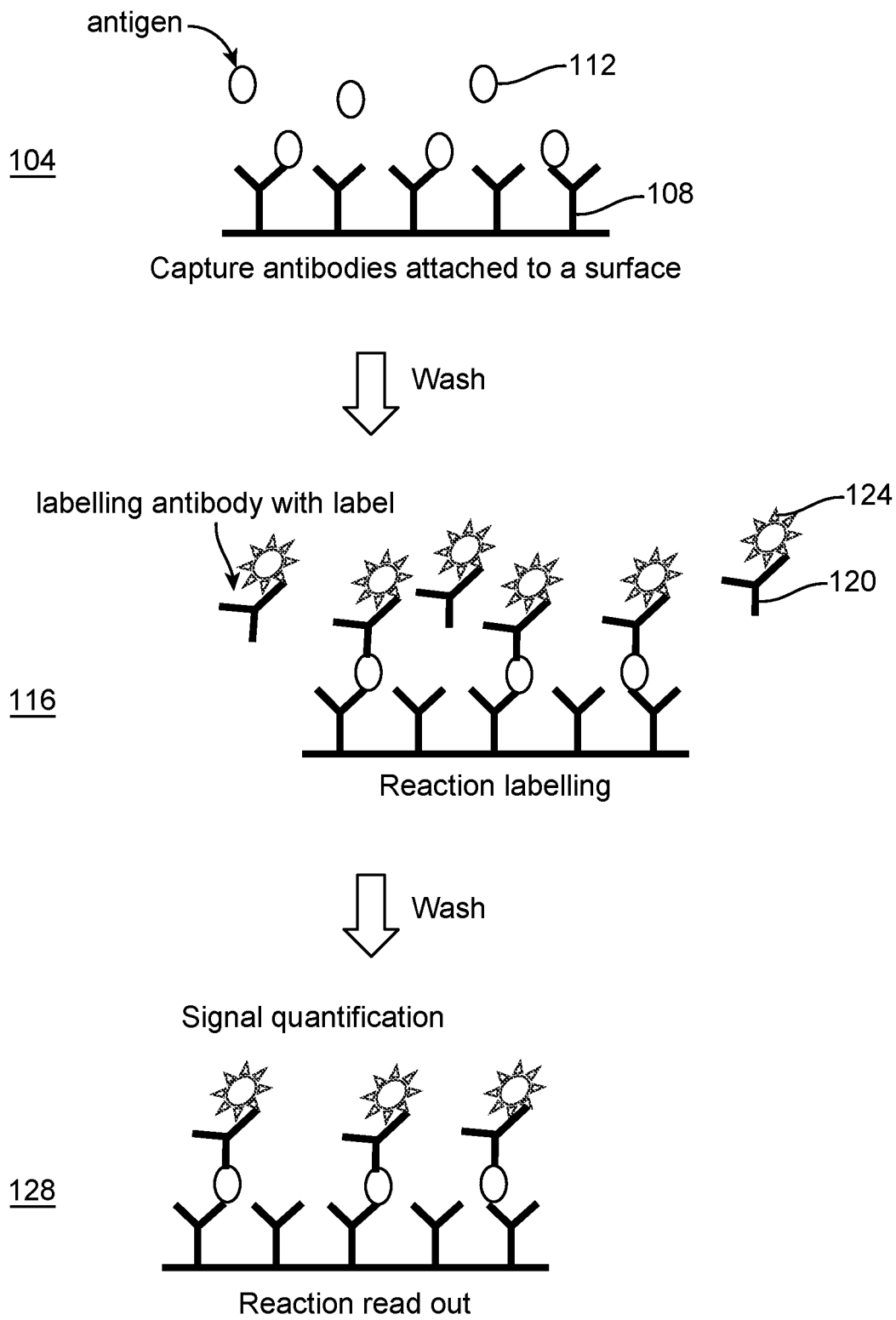
FIG. 1 shows an example of an immunoassay.

Current techniques of measuring kinetics of reactions (e.g., binding of an antigen to an affinity reagent) may involve interrupting a reaction to measure an amount at a specific time. Interrupting a reaction prevents real-time measurement of kinetics. Additionally, in order to obtain accurate and precise measurements, procedures may need to be followed rigorously. Errors from slight variations in procedure will result in inaccurate results, especially for fast reaction kinetics or measuring low concentrations of a reactant (e.g., an antigen).

Embodiments described herein include real-time measuring of the kinetics of reactions. Antigens, labels, affinity reagents, and beads may be mixed together in a batch reactor of a microfluidic chip. This time may be time to, the start of the reaction. A reaction may take place that may result in a bead being bound to a first affinity reagent, which is bound to an antigen, which is then bound to a second affinity reagent, which is bound to a label. A bead be attached to several first affinity reagents. Beads may be flowed out of the reactor continuously at a diagonal. A first bead may leave the reactor at time $t_1$. A second bead may leave the reactor at time t 2. A clean laminar flow may wash beads in a direction that intersects the diagonal. This flow may remove unbound labels, antigens, and/or affinity reagents from the beads. This clean laminar flow also may quench any reaction. The beads that remain in the diagonal flow may be bound to affinity reagents, antigens, and labels. The amount of labels of the beads may be measured in real-time at an output location.

For example, the label may be a fluorescent label, and the intensity of the fluorescent signal may be measured.

The time of the signal measurement may be adjusted by the time the beads take to reach the output location from the batch reactor. Amounts of bound antigen can then be plotted versus time. Concentrations (e.g., absolute or relative concentrations) and/or kinetic rate constants can be determined using the measured amount of labels and the times of the measurement.

Embodiments described herein may allow for an accurate assessment of the reaction kinetic through mathematically fitting of the antigen concentration over time. The confidence in the concentration fitting may be continuously calculated with each new bead being measured. The measurement may be ended, when the satisfactory confidence level is achieved from the real-time mathematical fitting.

Several thousand microbeads may be incubated in the immunoassay reaction. Less than 1,000 may be needed to achieve a high confidence kinetic profile of the reaction and yield a high accuracy measurement. The mathematical modeling of the reaction kinetic profile may achieve a high confidence concentration fitting after less than 5 minutes reaction for antigens in the nanomolar range, and less than 10 minutes in the picomolar range. Kinetics of binding reactions, dissociation reactions, and other reactions may be determined.

Systems and methods are described in further detail in this disclosure.

I. Reaction Kinetics

Figure 2:
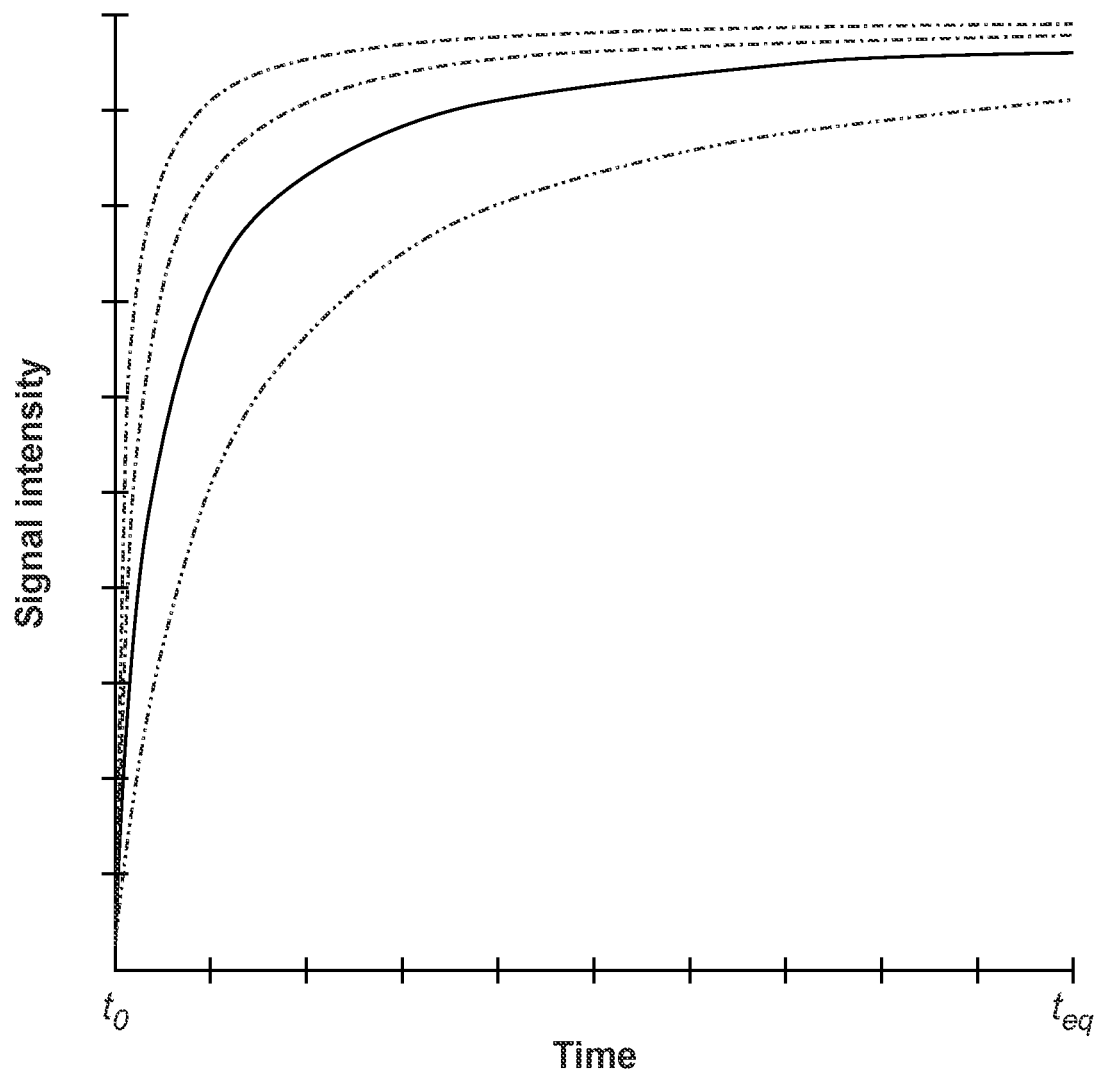
FIG. 2 shows a graph of a kinetic profile of a binding reaction.

FIG. 2 shows a graph of a kinetic reaction profile of a binding reaction with a given rate constant. The x-axis shows time. The y-axis shows signal intensity of a label indicating the completion of a binding reaction. The t0 at the bottom indicates the initial time. The $t_{eq}$ indicates the time at which the binding reaction is at equilibrium. The different lines correspond to different initial concentrations of a reactant, with a higher line being a higher initial concentration. The initial phase of the binding reaction has a high slope. Monitoring the initial phase rather than the equilibrium phase may allow for precise kinetic fitting and a quicker result.

Figures 3A, 3B:
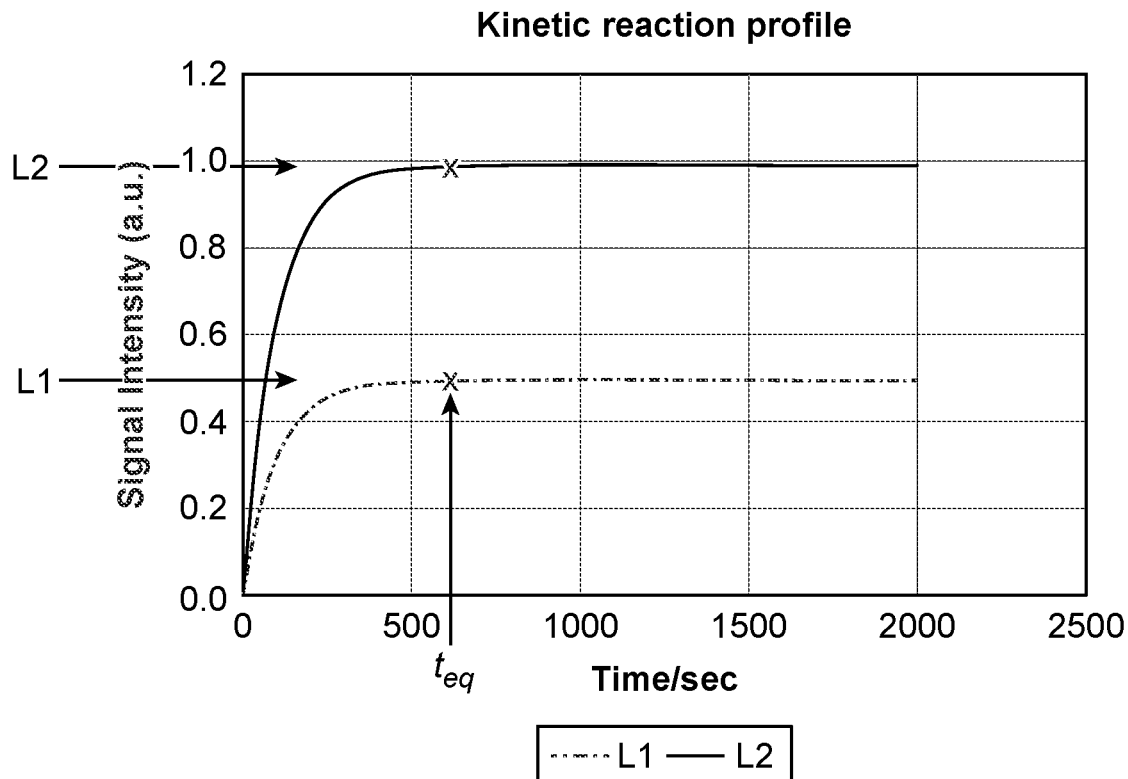
FIG. 3A shows an example kinetic reaction profile for a binding reaction according to embodiments of the present invention.
FIG. 3B shows a rate function established by the affinity constants of each binding entity according to embodiments of the present invention.

FIG. 3A shows an example kinetic reaction profile for a binding reaction. The x-axis shows the time in seconds. The y-axis shows the signal intensity of a label in arbitrary units. Line L1 is the profile for a first ligand (e.g., analyte, antigen) concentration. Line L2 is the profile for a second ligand concentration. In endpoint detection techniques, measurements may be delayed until the reaction reaches equilibrium (e.g., at time $t_{eq}$) to determine the concentration. As shown in FIG. 3A, the time may be around 10 minutes to reach equilibrium. Otherwise, measurements in the steep incline portion of the profiles should be rigorously carried out in order to be repeatable and comparable with other measurements.

FIG. 3B shows a rate function established by the affinity constants of each binding entity (i.e., affinity reagent). The equation includes the following variables: I is the signal intensity; $\mu S$ is the microbead concentration; A is the concentration of capture antibody (i.e., the concentration of the beads multiplied by the number of binding sites per bead); L is the concentration of the ligand from the sample that is being measured; $K_D$ is the dissociation constant of the complex; $k_{on}$ is the on rate constant of the complex; and t is the time of the reaction.

A transfer function converts a signal intensity value to a ligand/antigen concentration in the sample. With data of signal intensity as a function of time, the transfer function can use the rate function to determine the respective concentrations of each binding entity to the number of complexes being formed. However, when the reaction is interrupted at a set incubation time as with endpoint detection, the value of the ligand concentration is inferred from a calibration curve. The calibration curve would need to be determined from calibration samples and not from the test sample, and the calibration samples would need to be measured in the same manner as the test sample. Hence, using the rate function has advantages over endpoint detection in not needing a calibration performed.

With the kinetic reaction profile, the total ligand concentration can be calculated from fitting of the first few seconds of the reaction. By contrast, endpoint detection is typically performed at equilibrium, which may be minutes into the reaction.

Rate functions, such as in FIG. 3B, show that the ligand concentration can be calculated when the rate constants are known. Additionally, rate constants may be calculated when ligand concentrations are known. Both rate constants and ligand concentrations can be calculated from multiple experiments to generate multiple kinetic reaction profile curves.

II. Kinetic Immunoassay Technique

Calculating kinetic parameters using rate functions can be performed in the first few seconds of the reaction if the signals for a bound reaction for a given reaction time can be determined accurately.

A. Principles

Figure 4:
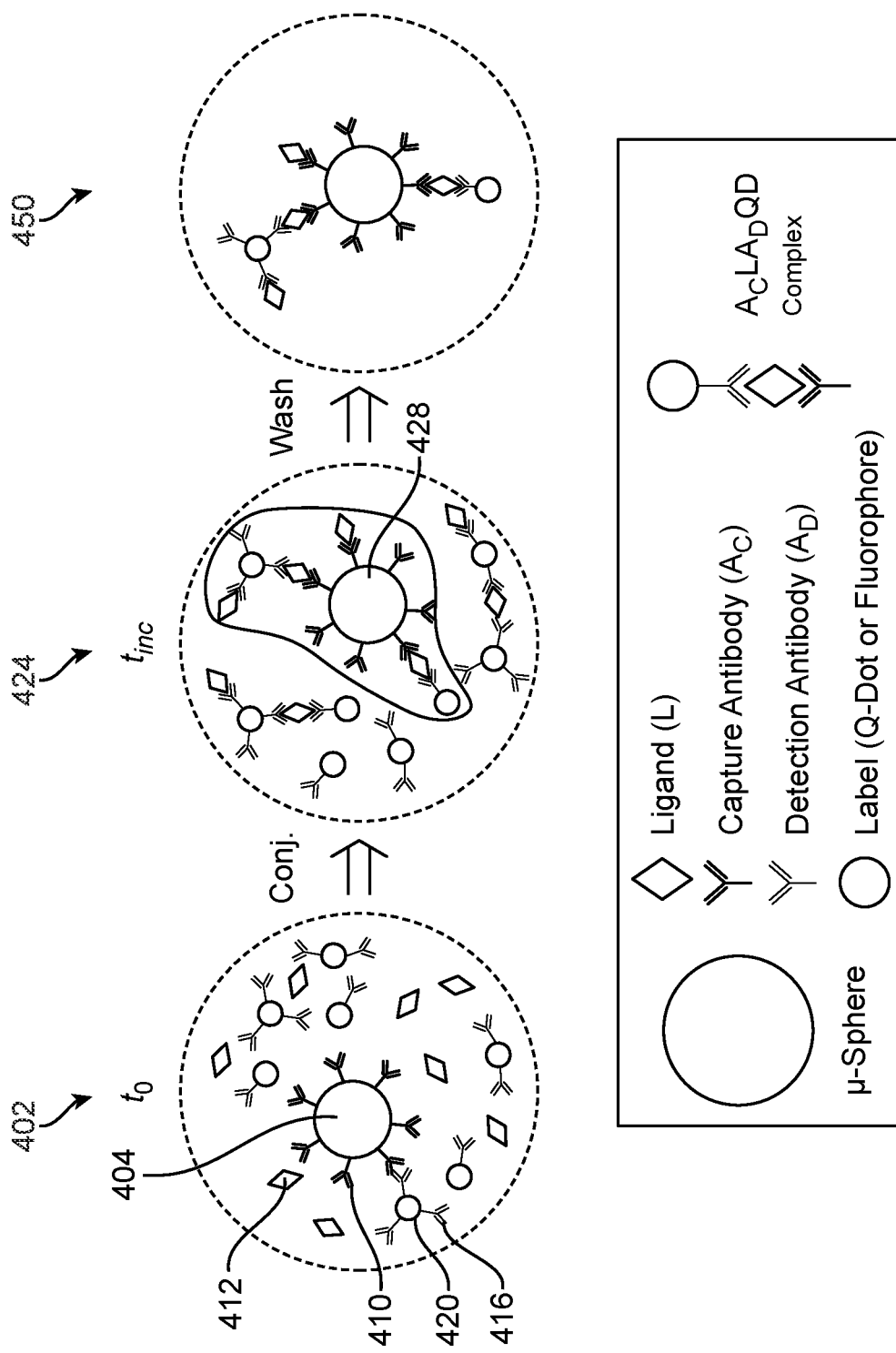
FIG. 4 illustrates mechanisms allowing for accurate determination of kinetic parameters according to embodiments of the present invention.

FIG. 4 illustrates the mechanisms allowing for accurate determination of kinetic parameters. Stage 402 shows time to. At stage 402, a capture bead 404 is present. Capture beads may be bound to capture antibodies, including antibody 410. Antigens, including ligand 412, may be present in the same mixture as the capture beads. Additionally, detection antibody, such as detection antibody 416 may be present. Detection antibody 416 may be bound to label 420. One or more detection antibodies may be bound to a single label. Label 420 may be a quantum dot, fluorophore, chemiluminescent tag, electrochemical label, or other suitable label.

Stage 424 shows the mixture after conjugation. At time $t_{inc}$ ("incubation time"), Ligands may bind to the detection antibody and/or the capture antibody. The expected binding reaction is a sandwich reaction, which forms a complex 428 of the capture bead bound to a ligand bound to a detection antibody with a label. Although FIG. 4 illustrates the capture bead with only seven capture antibodies, a capture bead may have 100 or more capture antibodies.

Stage 450 shows the mixture after washing the capture bead of ligands and detection antibodies bound to labels. Only the capture bead remains. The intensity of the labels therefore is related to the presence of bound ligands.

Figure 5:
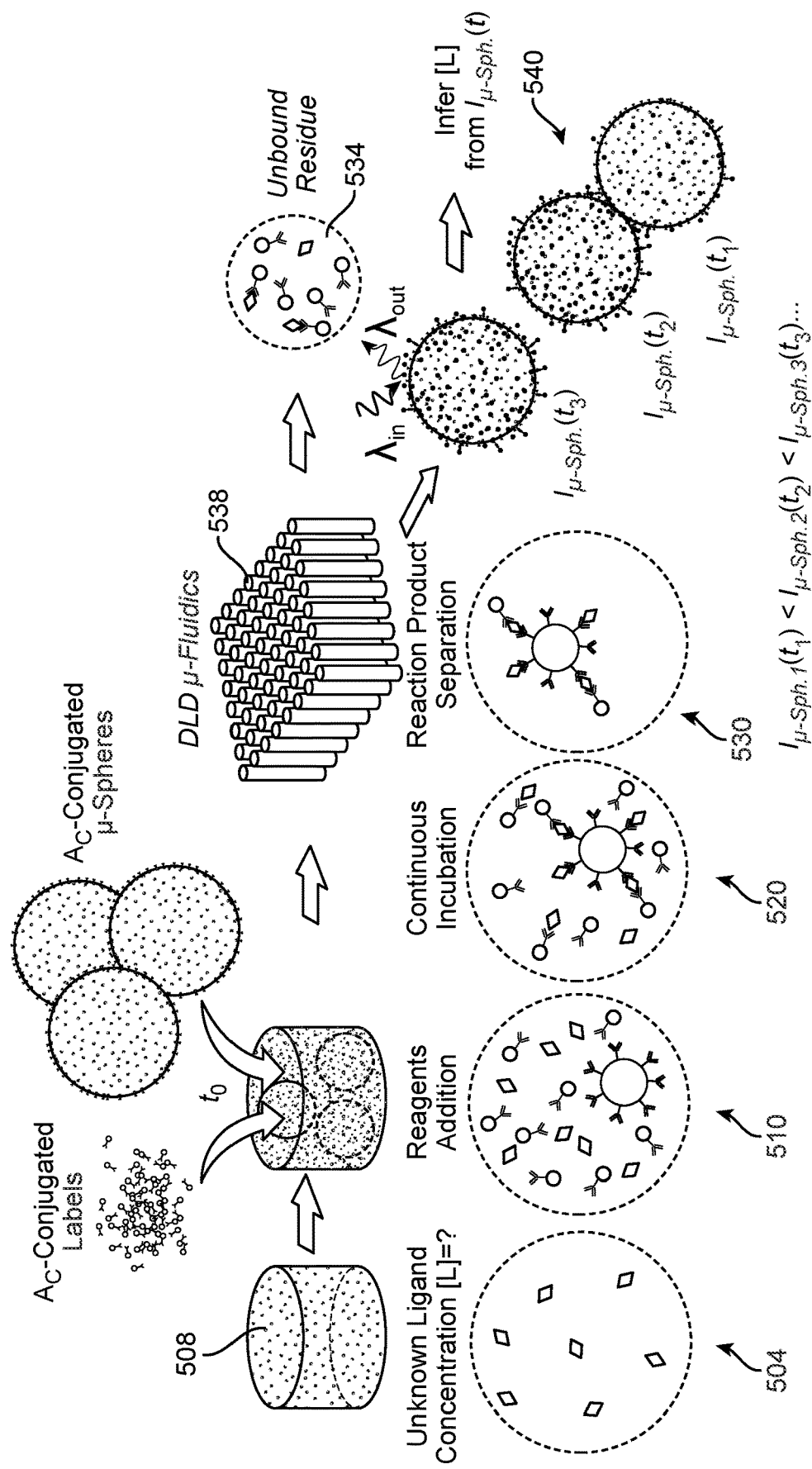
FIG. 5 shows steps in determining kinetic parameters according to embodiments of the present invention.

FIG. 5 shows steps in determining kinetic parameters using the components of FIG. 4. At stage 504, a reactor 508 may have an unknown ligand concentration. At stage 510, reagents are added at time to. Reagents include capture beads conjugated with capture antibodies and detection antibodies conjugated with labels.

Stage 520 shows continuous incubation. Reactions occur continuously in reactor 508 after time $t_0$.

Stage 530 shows a capture bead complex after removal of unbound residue 534, including ligands and detection antibodies conjugated with labels. The capture bead complex and unbound residue can be removed from reactor 508 at a distinct time (e.g., $t_1$, $t_2$, $t_3$). The separation of the capture bead complex from the unbound residue may be performed in a deterministic lateral displacement (DLD) microfluidics array 538.

As a result of a DLD array, a capture bead leaving the reservoir at time $t_1$ will reach a point first compared to a capture bead leaving at a later time $t_2$. A capture bead leaving at a later time $t_2$ will have a longer time for incubation and therefore more ligands and labels coupled to the bead. The intensity of beads at later times should be greater to reflect the greater number of ligands. Stage 540 shows that the initial unknown ligand concentration can be inferred from the intensities from capture beads over time.

Figure 6:
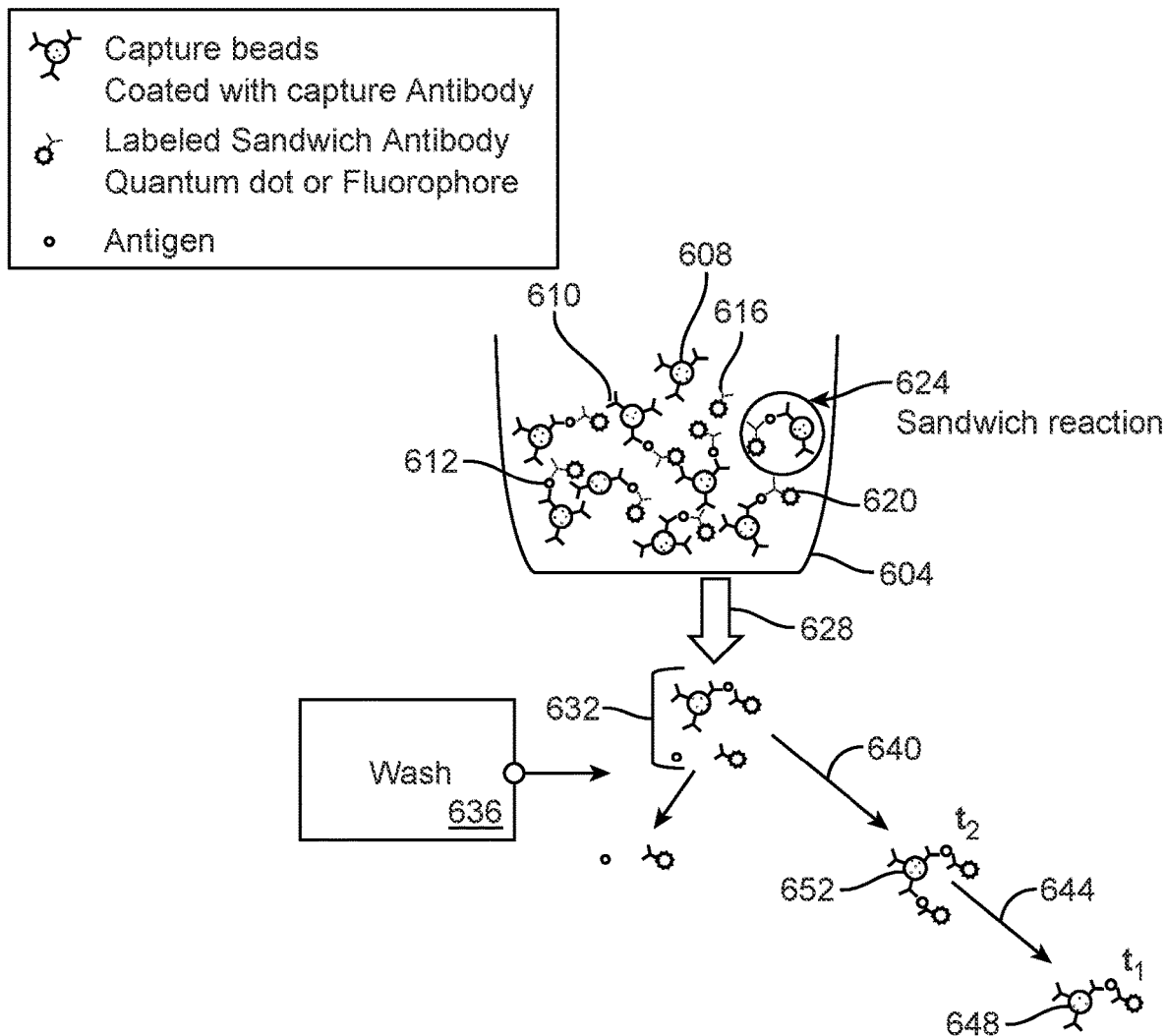
FIG. 6 shows a reactor and the mechanisms allowing for accurate determination of kinetic parameters according to embodiments of the present invention.

FIG. 6 shows another illustration of a possible reactor and mechanisms allowing for accurate determination of kinetic parameters. Reactor 604 contains capture beads, including capture bead 608. Capture beads may be bound to capture antibodies, including antibody 610. Capture beads may bind with an antigen, including antigen 612. Antigens may bind with a labeled sandwich antibody, including labeled sandwich antibody 616. The labeled sandwich antibody 616 includes label 620. Label 620 may be a quantum dot, fluorophore, chemiluminescent tag, electrochemical label, or other suitable label. The expected binding reaction is a sandwich reaction 624, which forms a complex of the capture beads bound to an antigen bound to a labeled sandwich antibody. The contents in the reactor may be incubated. Although FIG. 6 illustrates each capture bead with only three capture antibodies, a capture bead may have 100 or more capture antibodies.

Arrow 628 represents a flow of material out of reactor 604. Area 632 shows possible materials in the output of the reactor. The materials illustrated include the product of a sandwich reaction, as well as an unbound antigen and an unbound labeled sandwich antibody. The beads may be drawn out from reactor 604 at a constant rate over a fixed amount of time.

Wash 636 represents a flow that removes the unbound antigen and unbound labeled sandwich antibody from the product of the sandwich reaction. The capture beads are not removed by the wash and instead proceed in a direction indicated by arrow 640 and arrow 644, which are different from the direction of the wash. The wash direction may be from top to bottom in this figure rather than from left to right.

Bead 648 represents a capture bead that has had time $t_1$ in the reactor. Bead 652 represent a capture bead that has had time $t_2$ in the reactor, where $t_2$ is a longer time than $t_1$. Bead 648 is farther from reactor 604 than bead 652 because bead 648 left reactor 604 at an earlier time than bead 652. The same flow carries bead 648 and bead 652 so that bead 652 cannot pass bead 648. Bead 652 is depicted as a bead that has captured more than one antigen, each coupled to a labeled sandwich antibody. Bead 652 has spent longer in reactor 604 than bead 648 so bead 652 may capture more antigens.

The signal from the label or labels may be detected and quantified. The intensity of the signal may be related (e.g., proportional) to the amount of antigen on a bead. The signal intensity may be analyzed or plotted over time. A kinetic reaction profile can be determined from the signal intensity.

The error on each bead measurement may be controlled by the ensemble of molecules bound to the bead. The number of binding sites on each bead is known, and the number of ligands that should be bound to each bead may be mathematically known for any given time value. The error may be mathematically calibrated. For determinations of whether a concentration is above a threshold, a 99% confidence level may be achieved rapidly (e.g., within 5 minutes in the picomolar range). For example, a kinetic reaction profile may be used to determine whether the concentration of troponin I is above a threshold concentration that indicates a heart attack.

Figure 7A:
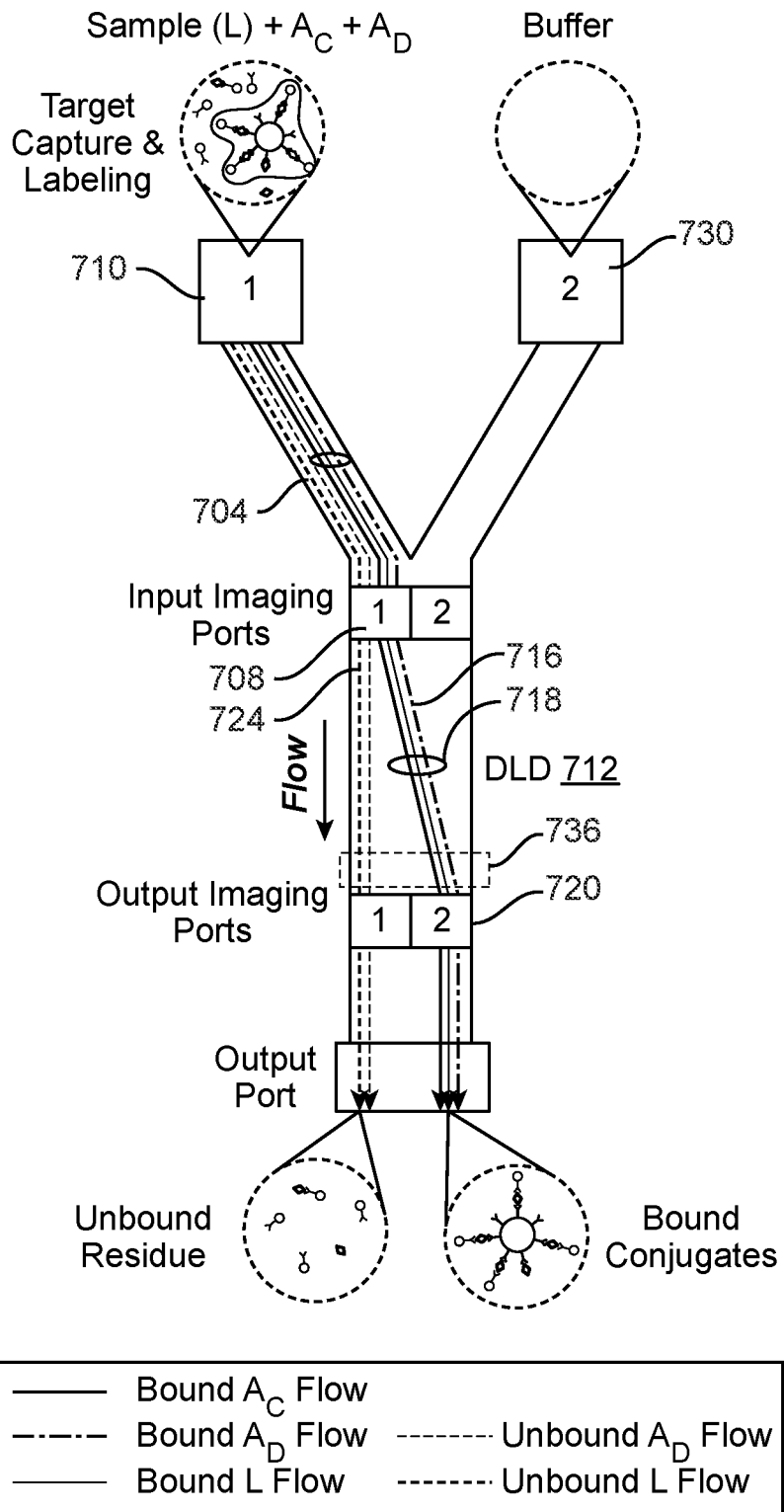
FIG. 7A illustrates a microfluidic chip for analyzing reaction kinetic parameters according to embodiments of the present invention.

FIG. 7A illustrates a microfluidic chip for analyzing reaction kinetic parameters. One or more channels (e.g., channel 704) may lead to imaging input area 708. The channels may be from a reactor 710 (e.g., reactor 508 in FIG. 5 or reactor 604 in FIG. 6) or from a reservoir for a wash solution. Imaging input area 708 allows for brightfield images of beads with labels and unbound labels to be taken. Imaging input area 708 is optional. FIG. 7A is not shown to scale.

After going through imaging input area 708, the bead mixture goes through deterministic lateral displacement (DLD) array 712. DLD arrays are described in U.S. Pat. No. 7,150,812, the entire contents of which are incorporated herein by reference for all purposes. DLD array 712 may include a plurality of structures. The structures may be pillars with a circular base or a rectangular (e.g., square) base. The structures may be in a regularly spaced array. The array may define straight paths through the structures. These straight paths may be offset from the path going from the channels through the imaging input area. The straight paths through DLD array 712 may not be parallel to the longitudinal axis of the chip. In FIG. 7A, the longitudinal axis is illustrated in the vertical direction.

The solid lines indicate paths (e.g., path 716) that the beads follow through the DLD array. These paths are at a diagonal from imaging input area 708. The beads travel and are displaced laterally from their input. Oval 718 indicates that the capture antibody, detection antibody, and ligand are bound together. The beads travel to imaging output area 720. Imaging output area 720 is laterally displaced from imaging input area 708.

The dashed lines indicate paths (e.g., path 724) that a cleaning flow may follow. This cleaning flow may be delivered from one or more channels. The cleaning flow may be from buffer reservoir 730. The cleaning flow may be along the longitudinal axis. The cleaning flow directs unbound antigens and antibodies away from the beads, effectively washing the beads. With the longitudinal direction of the cleaning flow, the cleaning flow may go to imaging output area 720, which is aligned with imaging input area 708. Although only a few solid lines are illustrated, the cleaning flow may cover most (50%, 60%, 70%, 80%, 90% or more) or the entirety of the DLD array, washing beads throughout their travel to imaging output area 720. Imaging output area 720 is for brightfield imaging and is optional.

At measurement area 736, the labels may be measured. Measurement area 736 may be a section of the structures. The beads follow consistent and predictable paths between structures, and signals from the labels of the beads can be reliably measured by an imaging device or other detector. For example, a high sensitivity quantitative CMOS camera may image microbeads and detect down to a single fluorescent or photoluminescent label. The cleaning flow may remove other labels to decrease or eliminate background signal. The cleaning flow may fully replace the liquid volume around each bead up to several hundred times.

The total immunoassay reaction may be as small as 1 μL, 5 μL, or 10 μL. The sampling of the reaction may be carried out on less than 5 microliters.

Figure 7B:
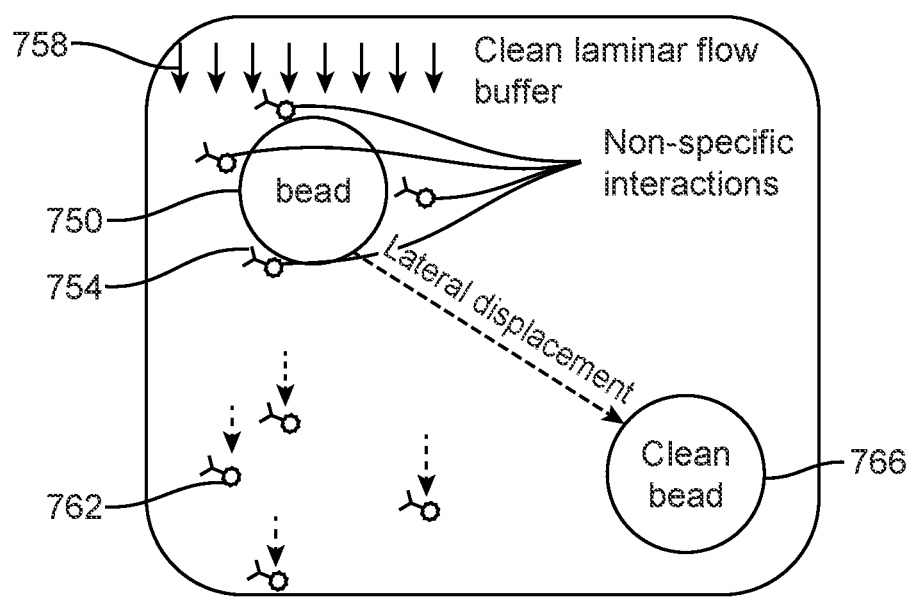
FIG. 7B illustrates the mechanics of the washing of the beads according to embodiments of the present invention.

FIG. 7B illustrates the mechanics of the washing of the beads. Bead 750 has non-specific interactions with labeled sandwich antibody 754 and other labeled sandwich antibodies. In this example, bead 750 is not bound to any antibodies and therefore is not bound to any antigens, which are therefore not bound to any labeled sandwich antibodies.

Arrows, including arrow 758, show laminar flow of a buffer solution. This flow cleans bead 750 of non-specific interactions. The flow of the buffer solution may be similar to path 724 in FIG. 7A. The flow may be in a direction parallel to the longitudinal axis of the microfluidic chip. The unbound labeled sandwich antibodies (e.g., labeled sandwich antibody 762) are washed away from bead 750 in the direction of the flow of the buffer solution.

Bead 750 is laterally displaced, which may be as explained with DLD array 712 in FIG. 7A. After lateral displacement, bead 766 may be clean with little or no labeled sandwich antibodies nearby (e.g., within a distance equal to the diameter of the bead).

Figure 8:
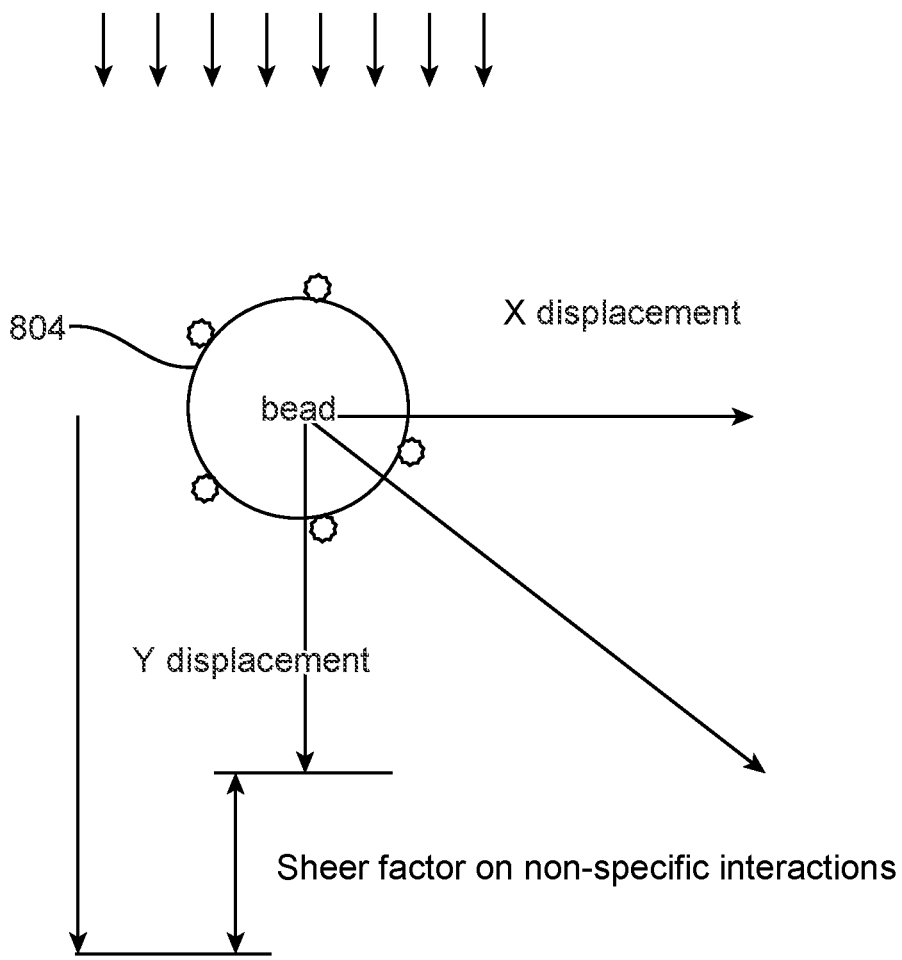
FIG. 8 depicts the relationship between sheer factor and displacement according to embodiments of the present invention.

FIG. 8 depicts the relationship between sheer factor and displacement. A laminar flow is in the y direction (vertical) in the figure. Bead 804 is displaced in both the y direction and x direction (horizontal) in traveling diagonally. Bead 804 is subjected to a Sheer factor, which is the force applied by the laminar flow on non-specifically bound entities. The Sheer factor is the difference between the vertical (y) velocity of bead 804 and the laminar flow. The x displacement determines how many times the liquid volume around the bead is fully renewed. In embodiments, a 6 μm bead that travels 5 mm in the x direction results in the buffer around the bead (i.e., any liquid in contact with the bead surface) being exchanged 833 times.

Figure 9C:
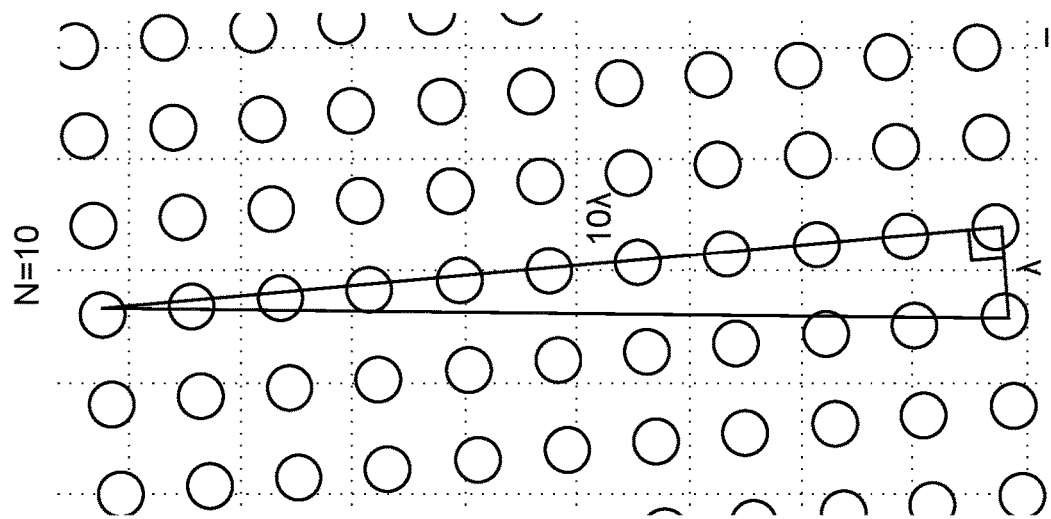
FIGS. 9A, 9B, and 9C show possible orientations of structures according to embodiments of the present invention.
Figure 9B:
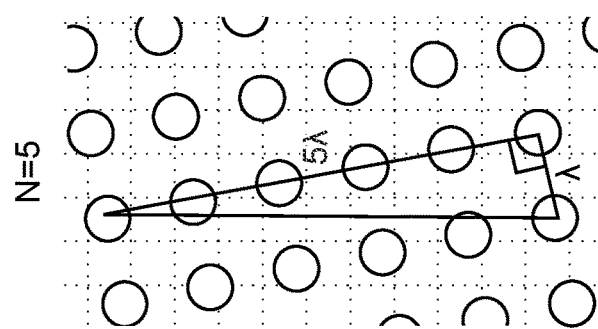
Figure 9A:
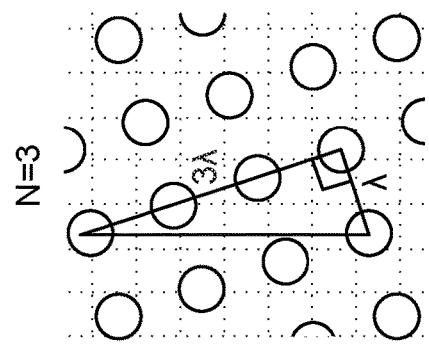

FIGS. 9A-9C illustrate possible orientations of structures. The structures are offset from the longitudinal axis of the microfluidic chip to create lateral displacement in the flow of the beads. FIG. 9A shows the largest offset angle, and FIG. 9C shows the smallest offset angle. FIG. 9A shows an orientation of structures where starting from a given structure, three additional structures are passed to reach a structure that is shifted one over to the left from the starting structure. The shift is denoted as λ, which is the distance from the center of one structure to the center of the adjacent structure. The angle of the offset can be calculated from $\tan^{-1}(1/3)$. The orientation is denoted as N=3, where 3 is the number of structures for a shift to the right. FIG. 9B shows an orientation of N=5. FIG. 9C shows an orientation of N=10.

A lower N value will result in larger diameter beads being shifted laterally but may not move smaller diameter beads laterally. The relationship between the critical diameter and the N value can be determined from an empirical equation:

$$\frac{D_C}{G} \cong \alpha \times \epsilon^\beta$$

$$\epsilon = \frac{1}{N}$$

$$D_C \cong \alpha G \times [\tan(\theta)]^\beta$$

where $D_C$ is the critical diameter of the beads, G is the gap distance between adjacent structures, N is the value described in FIGS. 9A-9C, θ is the angle of the rotational offset of a square lattice to arrive at the structures, and α and β are fitted parameters.

FIGS. 9A-9C show N as an integer, but N is not restricted to integer values. The structures may be a rotational offset of a square lattice by an angle θ. Angle θ is continuous and not limited to values where N is an integer.

The gap spacing, G, and the height of the structures may be any value greater than the diameter of the beads. In some embodiments, the gap spacing and/or the height of the structures may be 1.1 to 1.2, 1.2 to 1.3, 1.3 to 1.4, 1.4 to 1.5, 1.5 to 2, 2 to 3, 3 to 5, 5 to 10, 10 to 20, or greater than 20 times larger than the diameter of the beads.

B. Two-Step Conjugation

Some embodiments may include dividing the sandwich reaction into two steps. The first step may include binding the antigen to the capture bead via an antibody. The second step may include binding a label to the antigen-capture bead complex. The second step may be performed after the first step and in a different location than the first step.

A two-step conjugation may include several advantages over a single-step conjugation in certain embodiments. In some reaction schemes, a single-step conjugation may result in products other than a sandwich reaction complex of one label, one antigen, and one capture bead. As an example, an antigen may bond to a label without the antigen being bound to the capture bead. As another example, a single label may be configured to bind to multiple antigens. As a result, complexes may include one or more label compounds with multiple antigens, without a capture bead. Because these complexes are not immobilized on a capture bead, the antigens would not be detected. In some embodiments, labels may also bind to other proteins in a sample, which will reduce the number of labels and reduce the concentration of the desired sandwich reaction complex.

Figure 10:
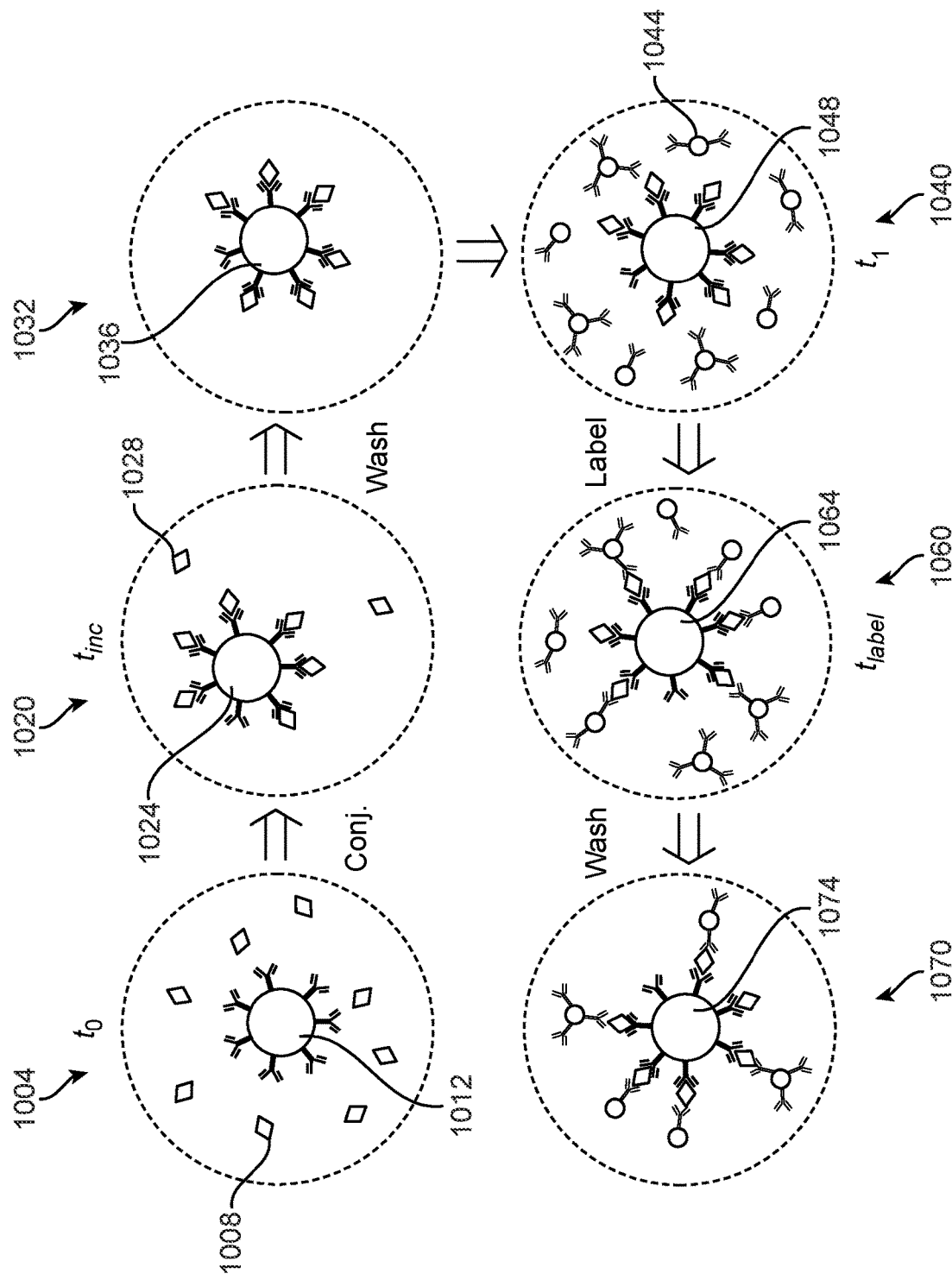
FIG. 10 illustrates an example of a two-step conjugation according to embodiments of the present invention.

FIG. 10 illustrates an example of a two-step conjugation. The first row shows the first step of target capture. The second row shows the second step of labeling.

Stage 1004 shows time t0. Ligands (e.g., ligand 1008) may be just introduced to the microspheres (e.g., bead 1012). The microspheres include several capture antibodies. Ligands may include antigens or any analytes described herein. Microspheres may include any capture bead described herein.

Stage 1020 shows a snapshot at time $t_{inc}$, after some time where the ligands can conjugate to the microsphere. Microsphere-ligand complex 1024 includes a microsphere bound to several ligands. Unbound ligands (e.g., ligand 1028) are present at stage 1020.

Stage 1032 shows a snapshot after the microspheres are washed of unbound ligands. Microsphere-ligand complex 1036 is free of unbound ligands.

Target capture in stages 1004 and 1020 of the first step can be described by the equilibrium reaction:

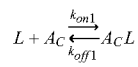

where L is the ligand concentration, $A_C$ is the capture antibody concentration, and $k_{on1}$ and $k_{off1}$ are rate constants.

Stage 1040 shows a snapshot at time $t_1$ after introducing labels (e.g., label 1044) to microsphere-ligand complex 1048. Labels include a detection antibody.

Stage 1060 shows a snapshot at time $t_{label}$ after labels are conjugated to the ligand. Sandwich complex 1064 includes labels bound to ligands.

Stage 1070 shows a snapshot after the sandwich complexes are washed of unbound labels. Sandwich complex 1074 is free of unbound labels.

The labeling in stages 1040 and 1060 can be described by the equilibrium reaction:

$$A_C L + A_D \underset{k_{off2}}{\overset{k_{on2}}{\rightleftharpoons}} A_C L A_D$$

where L is the ligand concentration, $A_C$ is the capture antibody concentration, $A_D$ is the detection antibody concentration, and $k_{on2}$ and $k_{off2}$ are rate constants.

Figure 11:
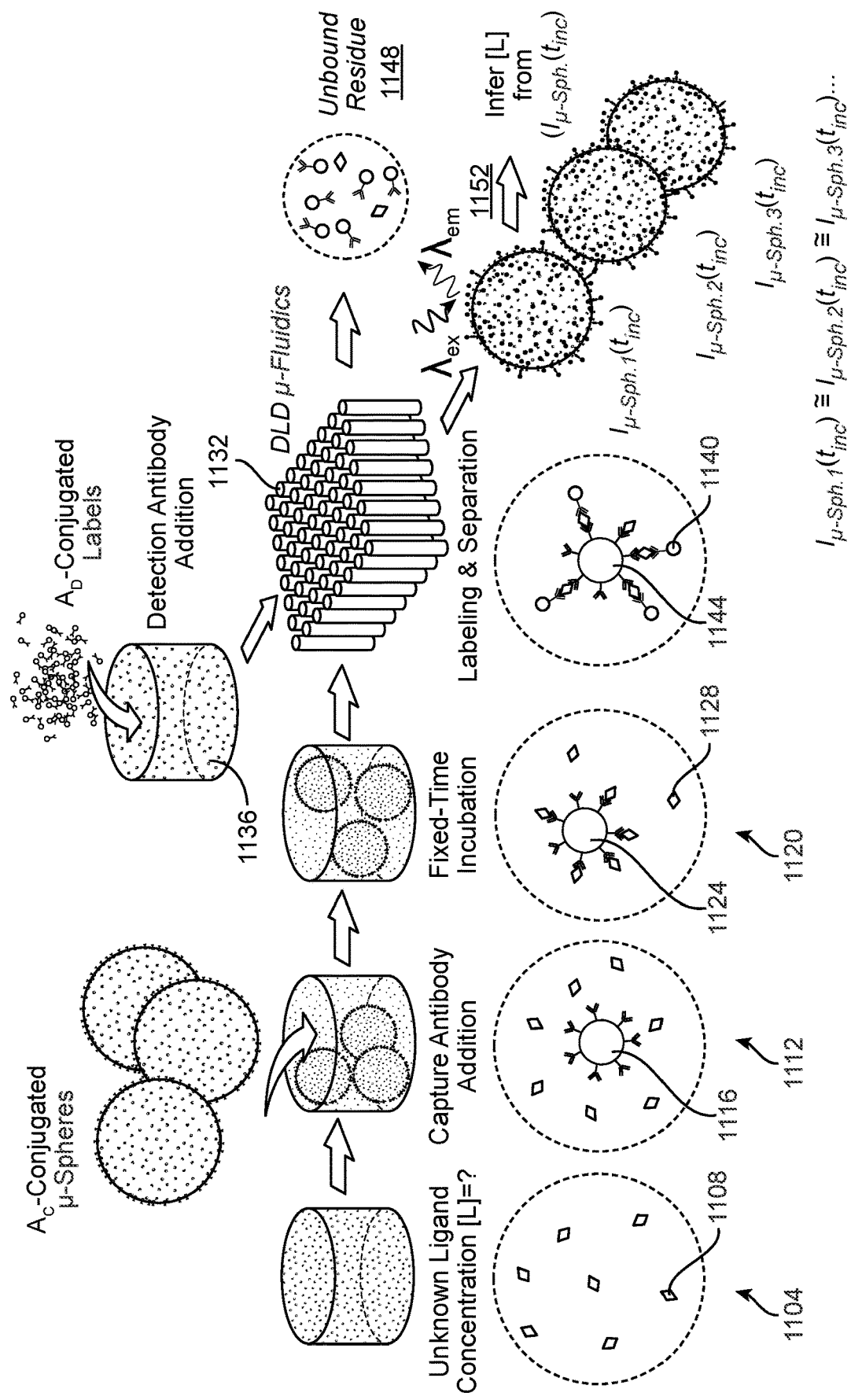
FIG. 11 illustrates an example of how a deterministic lateral displacement (DLD) array can be used for the two-step conjugation reaction according to embodiments of the present invention.

FIG. 11 illustrates an example of how a DLD array can be used for the two-step conjugation reaction. The washing of unbound ligands and labels occur during the flow of the conjugated microspheres through a DLD array.

Stage 1104 is the sample with an unknown ligand concentration [L]. The sample may include ligand 1108.

Stage 1112 shows a reactor after the addition of microspheres conjugated with a capture antibody (e.g., microsphere 1116). Stage 1112 is similar to stage 1020.

Stage 1120 shows the reactor after a certain duration of incubation. The reactor includes a microsphere-ligand complex 1124 and unbound ligands (e.g., ligand 1128).

The output of the reactor may be sent to a DLD array 1132. Additionally, detection antibody-conjugated labels may be added to DLD array 1132 from a reservoir 1136. The labels (e.g., label 1140) bind to ligands bound to the microsphere on sandwich complex 1144.

As a result flow dynamics through the DLD array, unbound residue 1148 is separated from microspheres, as described with FIGS. 4 to 7B.

Sandwich complexes including sandwich complex 1144 can be imaged at stage 1152. The concentration of the ligand can be inferred from a signal from the labels.

Figure 12:
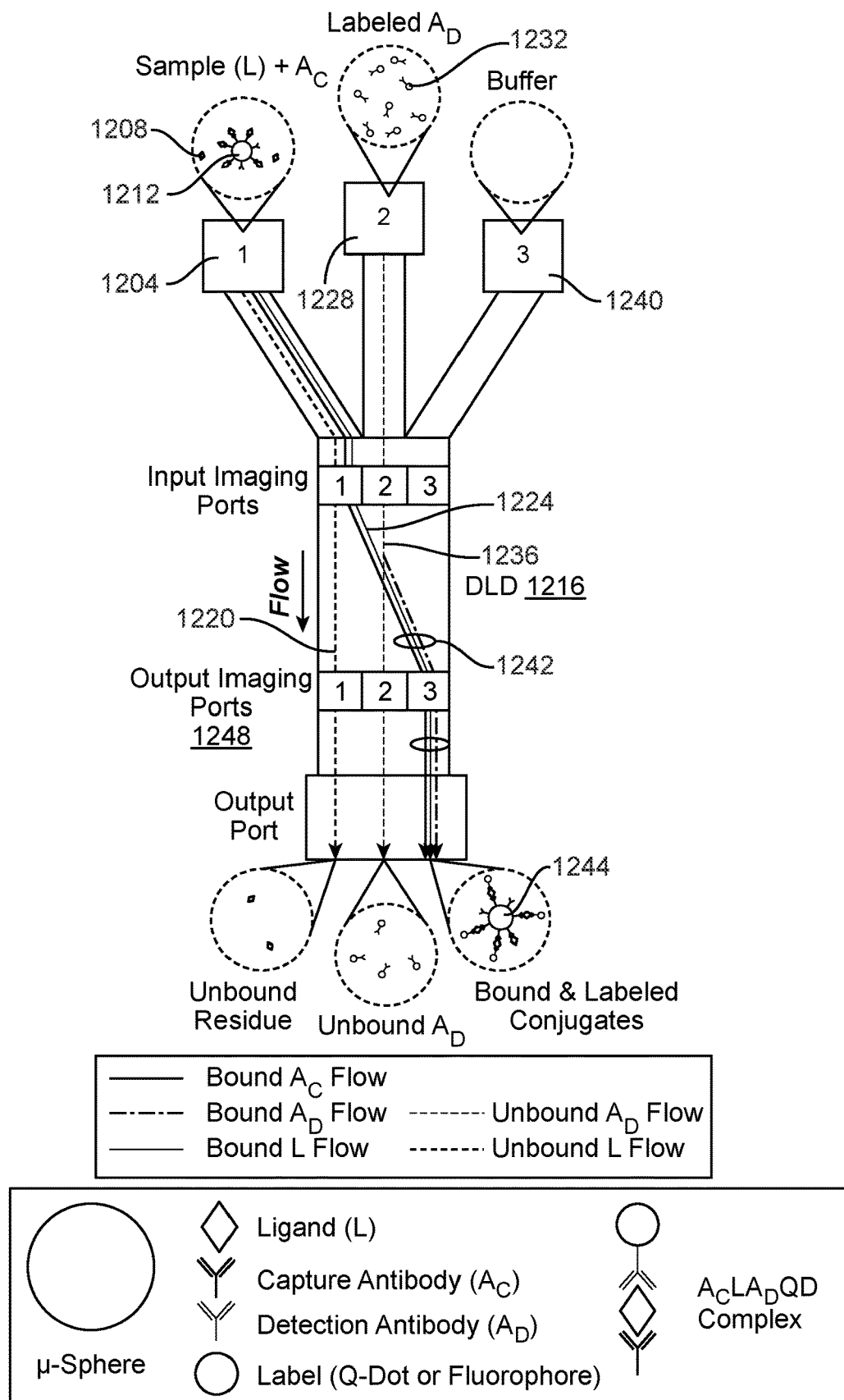
FIG. 12 illustrates an embodiment of the two-step conjugation in a DLD array according to embodiments of the present invention.

FIG. 12 illustrates an embodiment of the two-step conjugation in a DLD array. Reactor 1204 may include ligands (e.g., ligand 1208) and capture antibody-conjugated microspheres. The ligands may bind with the capture antibody-conjugated microspheres to form a ligand-microsphere complex (e.g., ligand-microsphere complex 1212). Reactor 1204 may also include unbound ligands (e.g., ligand 1208).

Flow with beads is drawn from reactor 1204 to DLD array 1216. Unbound ligands flow down path 1220, which may be parallel to the longitudinal axis of the microfluidic chip. The flow of unbound ligands may be aided by a buffer flow.

The ligand microsphere complexes may flow down a fluidic path 1224 defined by structures in DLD array 1216. The fluidic path may be offset from the longitudinal axis of the microfluidic chip.

A reactant reservoir 1228 may include detection antibody-conjugated labels (e.g., label 1232). The detection antibody-conjugated labels may flow down path 1236, which may be parallel to the longitudinal axis of the microfluidic chip. The labels may interact with ligand-microsphere complexes in fluidic path 1224. Labels may bind to the ligand-microsphere complex, forming a sandwich complex of a microsphere, ligand, and label. Unbound labels may continue down path 1236. The flow of unbound labels may be aided by a buffer flow.

A reservoir 1240 may contain a buffer. The buffer may flow down the longitudinal axis of the microfluidic chip. The buffer flow may aid the washing of the unbound ligands and/or labels from the microspheres. The buffer flow may be across the microfluidic chip and may not be limited to only a path going through input imaging port 3 and output imaging port 3.

Oval 1242 indicates that the capture antibody, ligand, and detection antibody are bound together in a sandwich complex. Sandwich complexes (including sandwich complex 1244) may be imaged at output imaging ports 1248. The signal intensity of the microspheres may be correlated with the number of labels on a microsphere, which may be correlated to the number of ligands on the microsphere.

III. Estimating Reaction Kinetic Parameters

Systems and methods described herein can be used to analyze kinetics of different reactions.

A. Dissociation Rate Constants

The dissociation rate constant ($k_{off}$) was estimated with methods and systems described herein. In this experiment, the sandwich immunoassay was performed with human C reactive protein (hCRP). The immunoassay was incubated until equilibrium, and then the beads were run through the DLD array. The washed beads were trapped in holding traps designed in the chip, and the signal decay was monitored over time on a few beads to detect the signal loss function.

Figure 13:
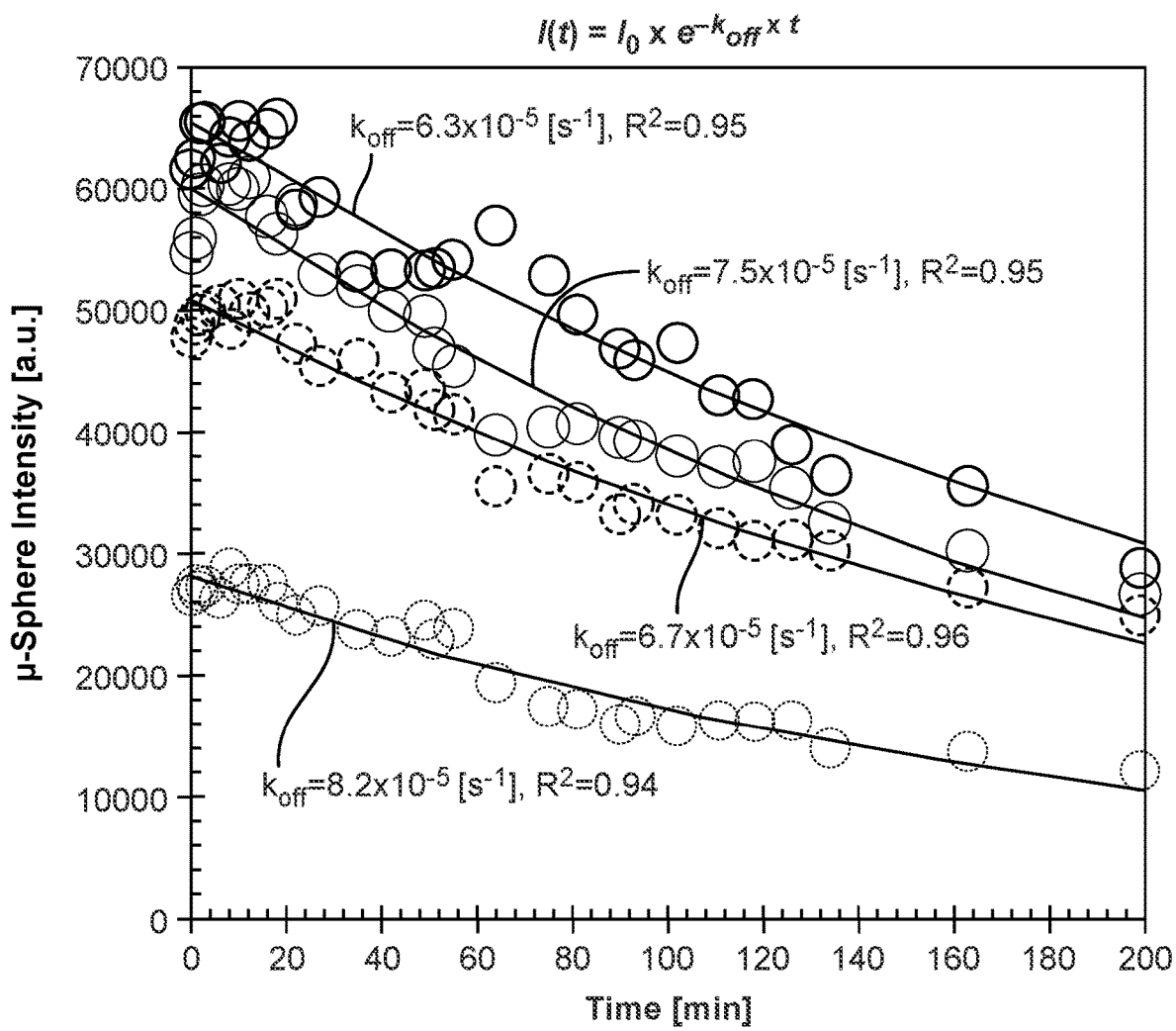
FIG. 13 shows a graph of reaction kinetic profiles generated with a DLD array according to embodiments of the present invention.

FIG. 13 shows a graph of reaction kinetic profiles generated with a DLD array and methods described herein. The x-axis shows time in minutes. The y-axis shows the signal intensity in arbitrary units. Each line corresponds to signal decay of a single microbead. All microbeads are from the same reaction, so are expected to have a similar $k_{off}$.

The intensity of labels as a function of time can be represented by:

$$I(t) = I_0 e^{-k_{off} \times t}$$

where $I_0$ is the initial intensity of the labels bound to microspheres, $k_{off}$ is the dissociation rate constant, and t is time.

The intensities at different times can be fit to the equation and $k_{off}$ can be determined. The determined $k_{off}$ are shown in FIG. 13. The fit shows that we have a single exponential fit, and this demonstrates that only sandwich bound signal is being detected, and the rate at which it decays corresponds to the known $k_{off}$ value for this antibody system. The $R^2$ values are provided, showing good fits to the data.

B. Multiplexing

Different size beads and/or different types of labels can be used to test examine kinetics of different reactions with the same assay.

Figure 14A:
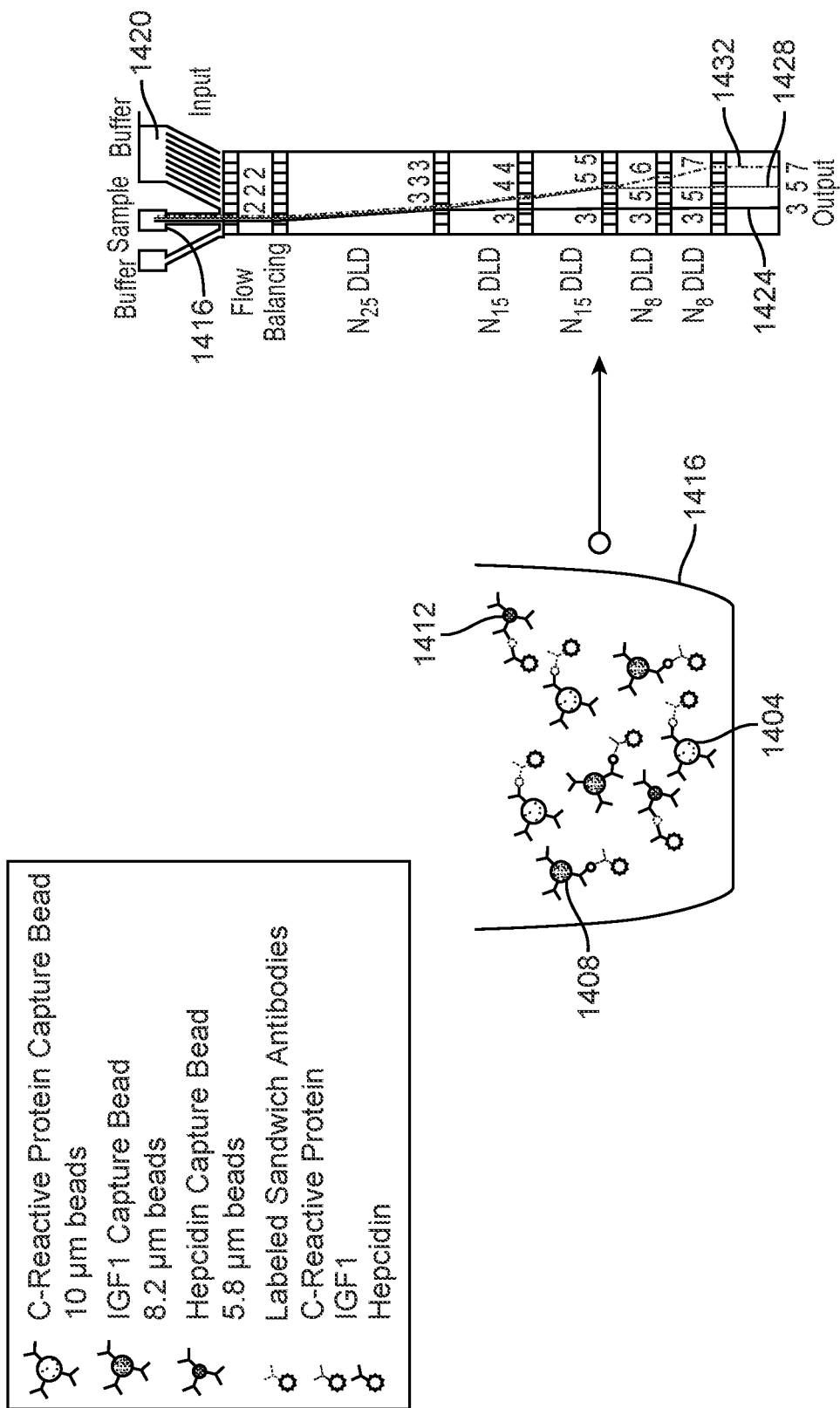
FIG. 14A shows an example of multiplexing using different size beads according to embodiments of the present invention.

FIG. 14A shows an example with different size beads. Bead 1404 is a 10 μm diameter bead, bound to an antibody that captures C-reactive protein. Bead 1408 is an 8.2 μm diameter bead, bound to an antibody that captures IGF1. Bead 1412 is a 5.8 μm diameter bead, bound to an antibody that captures hepcidin. These beads, along with C-reactive protein, IGF1, hepcidin, and labeled sandwich antibodies are incubated in reactor 1416.

Flow with beads is drawn from reactor 1416 through a series of DLD arrays. Buffer from buffer reservoir 1420 is flowed to wash the beads to remove non-specific interactions as described herein. The series of DLD arrays separates the different size beads laterally. The DLD arrays are denoted as $N_m$, where m denotes the number of additional rows of pillars corresponding to a one-column shift in beads (indicated by N in FIGS. 9A-9C). The smallest beads (e.g., bead 1412) follows path 1424. The medium beads (e.g., bead 1408) follows path 1428. The largest beads (e.g., bead 1404) follows path 1432.

Figure 14B:
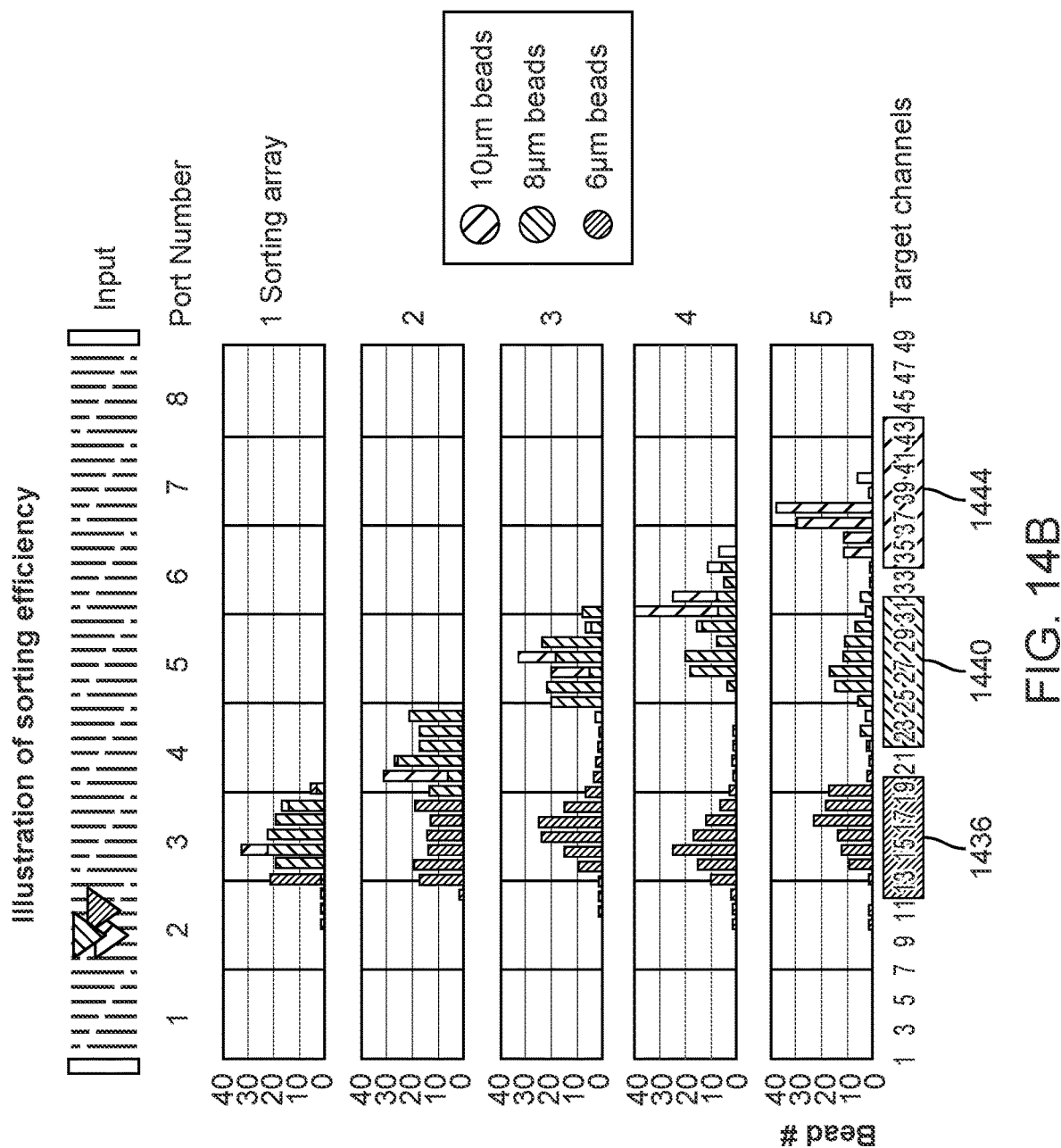
FIG. 14B shows the distribution of beads at different locations in the microfluidic chip according to embodiments of the present invention.

FIG. 14B shows the distribution of beads at different locations in the microfluidic chip. The smallest beads, bead 1412, are displaced the least amount laterally, ending in port 3 and target channels 13-19 (indicated by box 1436). Bead 1408 is displaced an intermediate amount laterally, ending mostly in port 5 and target channels 23-31 (indicated by box 1440). The largest beads, bead 1404, is displaced the largest amount laterally, ending mostly in port 7 and target channels 35-43 (indicated by box 1444).

The results show that different size beads can be used to analyze the kinetics or concentrations of different antigens at the same time.

C. Signal Intensity Versus Time

The signal intensity was tracked over time using methods and systems described herein. The beads are attached to streptavidin. Biotin is labeled with quantum dots. Streptavidin has a high affinity to bind with biotin.

Images of beads having reaction times of 1 min., 8 min., and 23 min. show brighter (i.e., higher signal intensity) beads with longer reaction times.

Figure 15:
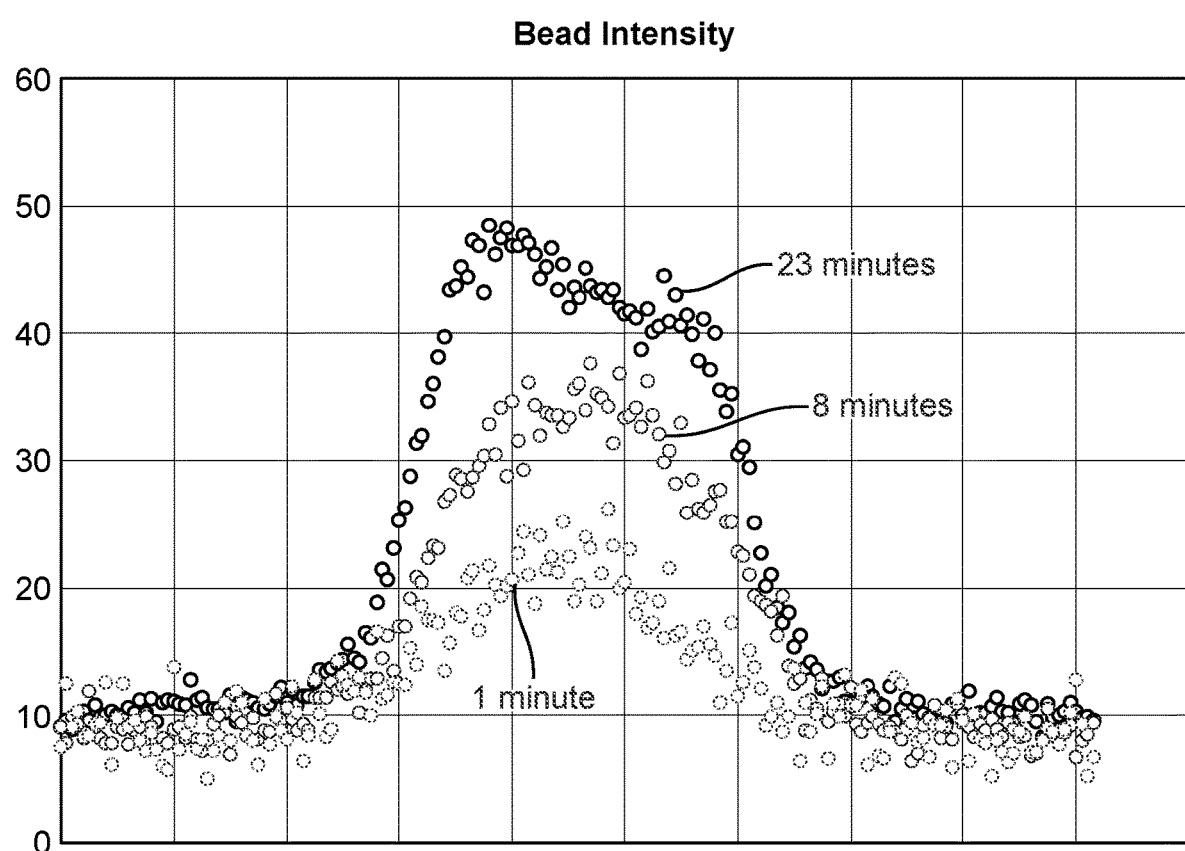
FIG. 15 is a graph of the bead intensity according to embodiments of the present invention.

FIG. 15 is a graph of the bead intensity. The x-axis is the x-coordinate (e.g., left to right in FIG. 7A) of the pixel. The x-axis spans 450 pixels. The y-axis is the sum of the signal intensities from all pixels at a given x-coordinate. FIG. 15 shows that higher reaction times lead to higher signal intensities from the beads.

Figure 16:
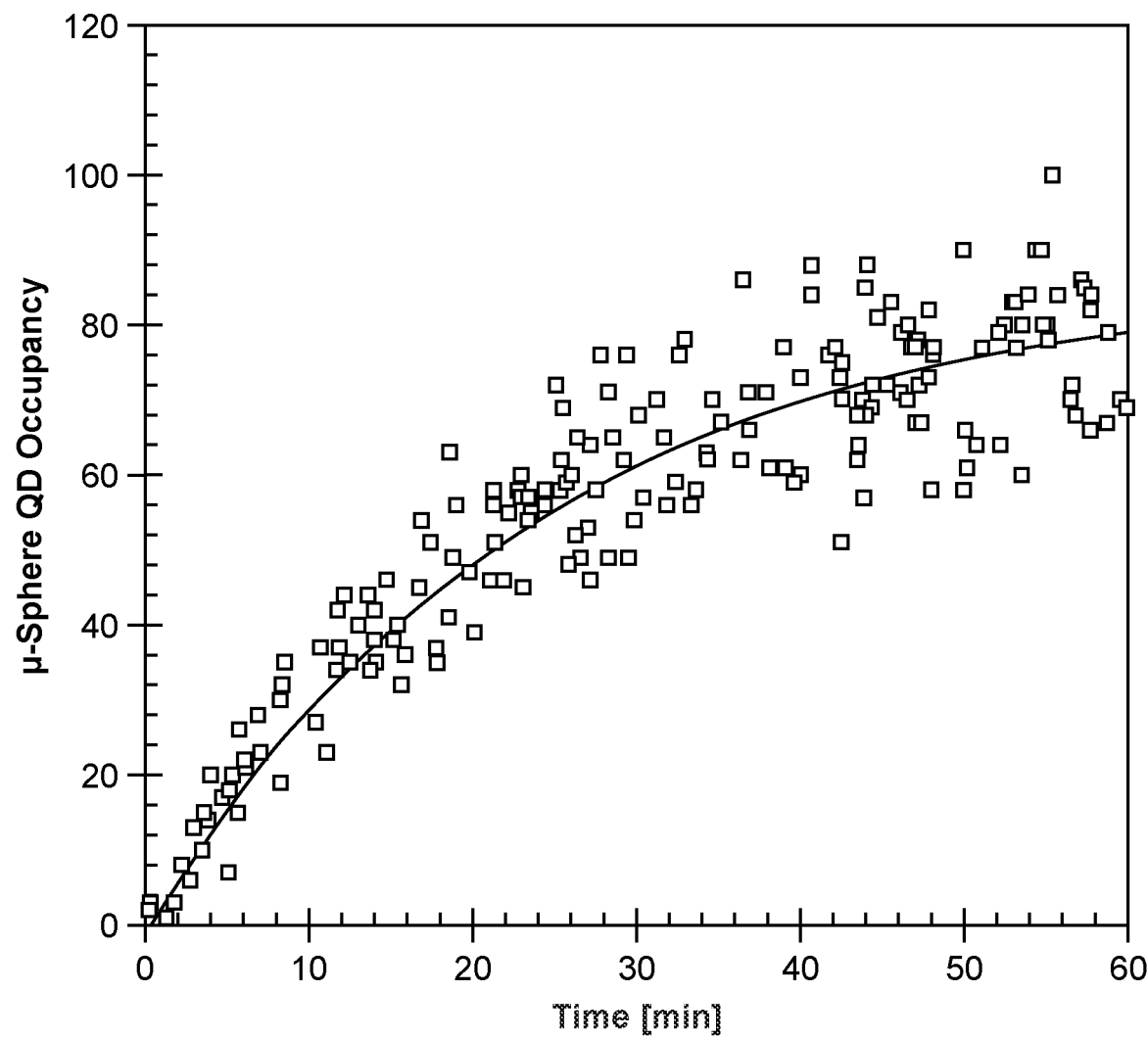
FIG. 16 shows a graph of signal intensities over time according to embodiments of the present invention.

FIG. 16 shows a graph of signal intensities over time for 10 μm beads modified with streptavidin and biotin labeled with quantum dots. The x-axis is time in minutes. The y-axis is microsphere quantum dot occupancy, which represents the number of dots on the surface of the bead and is a signal intensity. The reaction is run three times to generate the data points in the graph. The fitted line is for illustrative purposes. The graph shows a kinetic reaction profile. The profile has a steep increase then levels off as the reaction approaches equilibrium.

D. Kinetic Measurements

An experiment verified the capability of methods and systems described herein to analyze reaction kinetics in the picomolar concentration range.

Figure 17:
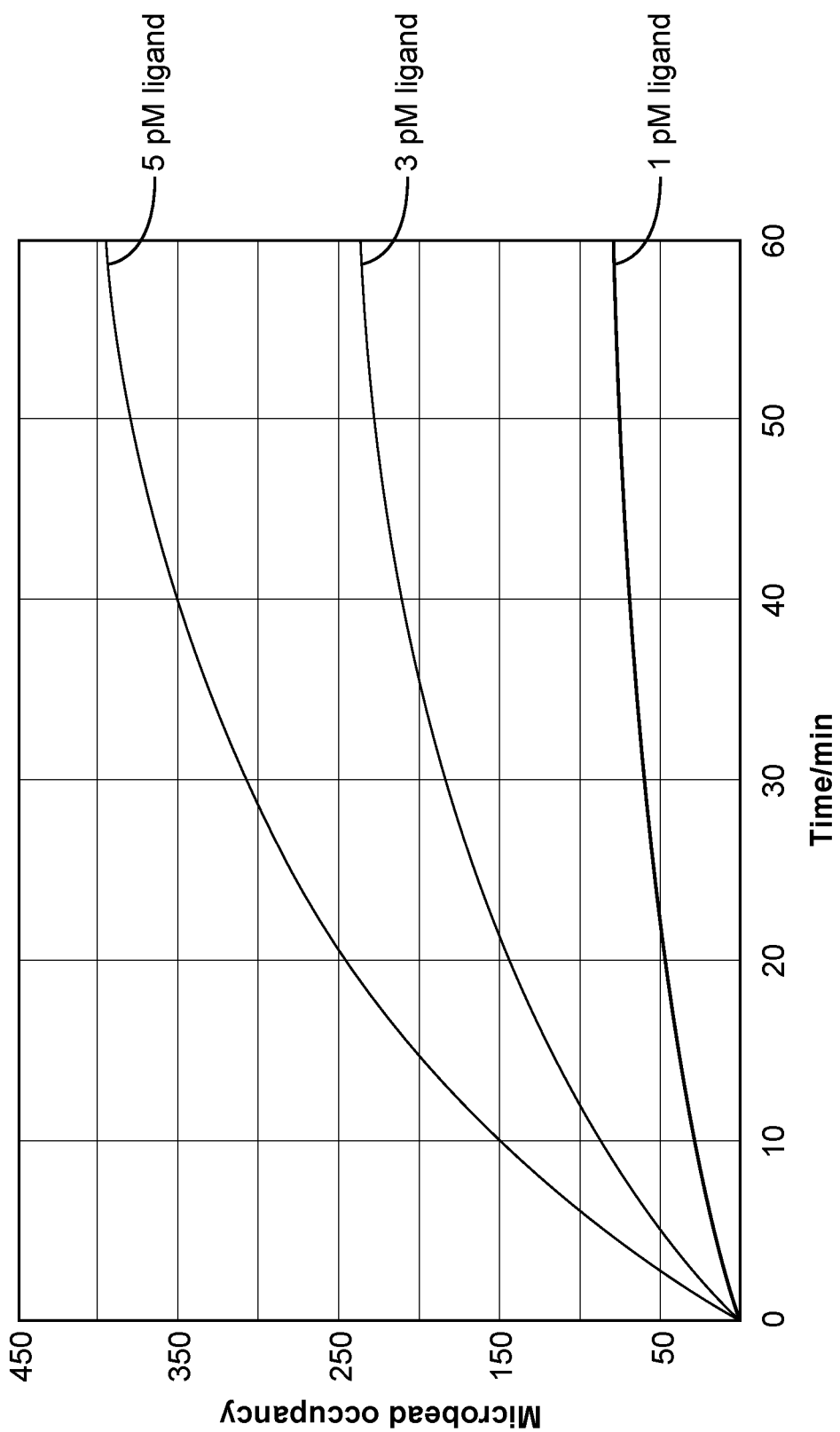
FIG. 17 shows a graph of reaction profiles with different ligand concentrations according to embodiments of the present invention.

FIG. 17 shows a graph of reaction profiles with different ligand concentrations in the picomolar range. The x-axis is time in minutes. The y-axis is microbead occupancy. The three lines are fitted lines for different concentrations of ligands: 1 pM, 3 pM, and 5 pM. The 5 pM ligand has the steepest increase and the highest occupancy near equilibrium. The 1 pM ligand has the least steep increase and the lowest occupancy near equilibrium.

Data in this graph can be analyzed to determine rate constants for the reaction. Additionally, data can be used for calibration for additional experiments. The concentration of a sample can be determined based on how closely the kinetic profile matches previous reaction data.

E. Conjugation Reaction Model

A conjugation reaction model helps understand the reaction profiles in methods and systems described herein. The conjugation reaction model is determined using a Langmuir reaction model. There is no analytical solution to the general sandwich assay reaction model. The differential equation is solved numerically to find the relationship between the number of ligands and the number of sandwich complexes of ligand, capture antibody, and label antibody.

FIG. 18 shows approximate solutions for experimentally relevant limiting cases for single-step conjugation, where $A_1$ is the primary (capture) antibody, L is the ligand, $A_2$ is the secondary (label) antibody, and $N_x$ is the number of x. The solutions are for $f_{bl}(t)$, which is the fraction of primary antibodies occupied with ligands that are also labeled with secondary antibodies as a function of time. For example, bead 1804 has an $f_{bl}$ of 4/7. Bead 1804 has seven primary antibody sites with five occupied with a ligand, and with four of the five ligands labeled with the secondary antibody.

Equation 1808 describes the fraction bound and labeled for conventional binding or non-depleting regime, where $[L] \sim [A_2] \ggg [A_1]$.

Equation 1812 describes the fraction bound and labeled in titration or strongly-depleting regime, where $[A_1] \sim [A_2] \gg [L]$. $f_{bl}(t)$ is proportional to [L].

Equation 1816 describes a mode suitable for rare biomarker detection, where $[A_2] \gg [A_1] \sim [L]$. The secondary antibody can be introduced in excess of $A_1$ and L.

Section 1820 describes variables in the equations.

IV. Example Methods

A. General Conjugation

Figure 19:
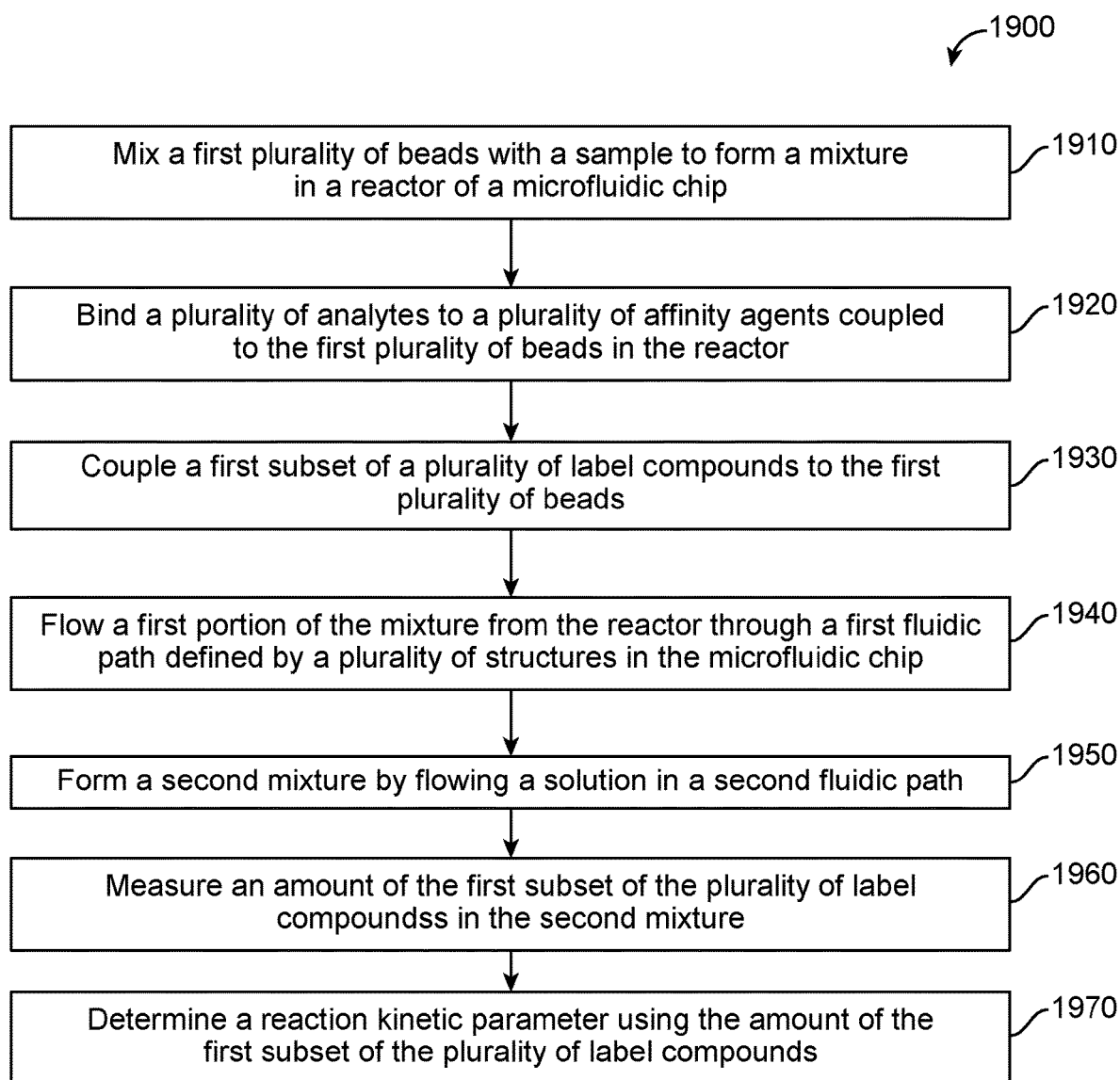
FIG. 19 is a flowchart of an example process for analyzing reaction kinetics according to embodiments of the present invention.

FIG. 19 is a flowchart of an example process 1900. In some implementations, one or more process blocks of FIG. 19 may be performed by a system, including system 1500 or any system described herein.

At block 1910, a first plurality of beads is mixed with a sample to form a mixture in a reactor of a microfluidic chip. The beads may include polystyrene, iron-oxide, silica, polymer, metal (e.g., gold, silver), or any other suitable material. The sample may include a plurality of analytes and a plurality of label compounds. Each bead of the first plurality of beads may be coupled to an affinity reagent. The analyte may be any analyte or ligand described herein. The affinity reagent may be configured to bind to the analyte. Each bead may be coupled to a plurality of affinity reagents. The plurality of label compounds may be configured to bind to the analyte. The label compounds may be a labeled sandwich antibody, as described herein, which may include a detectable label and an antibody configured to bind the analyte. The plurality of beads may be spherical.

The sample may be prepared using a biological sample obtained from a subject. The biological sample may include blood, plasma, serum, urine, tissue, sweat, nasal excretions, or material from a mouth swab. In some embodiments, the biological sample may be from a subject that has a tumor. The sample may be prepared by extracting or concentrating analytes from the biological sample. In some embodiments, the sample may exclude extracting or concentrating analytes.

The analyte may be an antigen. The antigen may be associated with a disease or a disorder. The antigen may be a protein. The antigen may have a concentration from 0 to 10 pM, 10 to 50 pM, 50 to 100 pM, 100 to 500 pM, 500 pM to 1 μM, 1 to 10 μM, 10 to 50 μM, 50 to 100 μM, or 100 to 500 μM. The antigen may be troponin I, C-reactive protein, IGF1, hepcidin, or any antigen described herein.

In some embodiments, the analyte may be a nucleic acid molecule. For example, the nucleic acid molecule may be DNA or RNA (e.g., mRNA). The nucleic acid molecule may be a biomarker for a disorder or disease. The nucleic acid molecule may be single-stranded.

The affinity reagent may be an antibody. The antibody may have an affinity to bind with a protein that is the antigen.

In some embodiments, the affinity reagent may be an oligonucleotide. The oligonucleotide may include a sequence of nucleotides complementary to a portion or all of the nucleic acid molecule analyte. The portion may be at least 3, 4, 5, 6, 7, 8, 9, 10, 10 to 15, 15 to 20, or 20 to 30 nucleotides. In some embodiments, the entire sequence of the nucleic acid molecule is complementary to a subsequence of nucleotides in the oligonucleotide.

Each label of the plurality of label compounds may be a fluorescent label, a quantum dot, a chemiluminescent label, or an electrochemical label.

In some embodiments, the label compound may include an oligonucleotide that includes a sequence of nucleotides complementary to a subsequence of the nucleic acid molecule analyte. For example, a first part of the nucleic acid molecule analyte may hybridize with the oligonucleotide attached to the bead, and a second part of the nucleic acid molecule analyte may hybridize with the oligonucleotide of the label compound.

In some embodiments, the label compound may include an enzyme. The enzyme may target double-stranded nucleic acid molecules. In this manner, the enzyme may recognize a nucleic acid molecule that has hybridized with an oligonucleotide attached to a bead.

At block 1920, the plurality of analytes is bound to a plurality of affinity agents coupled to the first plurality of beads in the reactor. Other analytes may be unbound in the reactor at that point in time. At later times, other analytes may bind to other affinity reagents of other beads in the reactor.

At block 1930, a first subset of the plurality of label compounds is coupled to the first plurality of beads. Coupling may occur in the first fluidic path or in the reactor. Coupling may be by binding the plurality of label compounds to the plurality of affinity agents that are bound to the plurality of beads. Coupling the first subset of the plurality of label compounds to the plurality of analytes may occur before or after binding the plurality of analytes to the plurality of affinity reagents. For example, the plurality of label compounds may bind to the analytes before the analytes are bound to the plurality of affinity reagents.

At block 1940, a first portion of the mixture is flowed from the reactor through a first fluidic path defined by a plurality of structures in the microfluidic chip. The first portion of the mixture may include the first plurality of beads coupled to the first subset of the plurality of label compounds. The plurality of analytes and the plurality of affinity agents (and optionally the plurality of label compounds) may be in the reactor for a predetermined incubation time. After an incubation time, a flow out of the reactor may be started. In some embodiments, the predetermined incubation time may be 0 seconds, 0 to 10 seconds, 10 to 30 seconds, 30 seconds to 1 minute, or greater than 1 minute.

The plurality of structures may include a plurality of pillars. The plurality of pillars may be a portion of an array of pillars. The array of pillars may be a DLD array, including any described herein. The array of pillars may be characterized by a plurality of rows and a plurality of columns. The plurality of pillars may include pillars from at least five columns from the plurality of columns. In some embodiments, the plurality of pillars may include from 1 to 5 columns, from 5 to 10 columns, from 10 to 20 columns, from 20 to 30 columns, from 30 to 50 columns, or more than 50 columns from the plurality of columns. The structures in the plurality of structures may be identical.

The microfluidic chip may have a longitudinal axis. The first fluidic path and the longitudinal axis may form an angle in a range from 10 degrees to 60 degrees. For example, the angle may be in a range from 10 to 20 degrees, from 20 to 30 degrees, from 30 to 40 degrees, from 40 to 50 degrees, or from 50 to 60 degrees. The first fluidic path may be in a diagonal direction relative to the microfluidic chip. The first fluidic path may be determined by the average (e.g., mean, median, or mode) direction of the first plurality of beads. The angle formed may be an angle calculated with FIGS. 9A to 9C. For example, the angle may be equal to or within 5% or 10% of $\tan^{-1}(1/N)$, where N may be any number from 0.1 to 30.

At block 1950, a second mixture is formed by flowing a solution in a second fluidic path. The second fluidic path may intersect the first fluidic path. The first fluidic path and the second fluidic path may intersect at an angle in a range from 10 to 20 degrees, from 20 to 30 degrees, from 30 to 40 degrees, from 40 to 50 degrees, or from 50 to 60 degrees. The second fluidic path may be parallel to the longitudinal axis. The second fluidic path may be determined by the average (e.g., mean, median, or mode) direction of the solution. The initial direction of the second fluidic path may be in the same initial direction as the initial flow from the reactor to the plurality of structures. The solution may include phosphate buffer saline (PBS).

Process 1900 may further include removing a second subset of the plurality of label compounds from the first portion of the mixture to form a second mixture including the first plurality of beads. The removal may be performed using the solution. The second subset of the plurality of label compounds may not be coupled to the first plurality of beads. The solution may wash or clean the beads of non-specific interactions as described herein.

Process 1900 may include removing unbound analytes. The plurality of analytes may be a first plurality of analytes. The method may further include removing a second plurality of analytes, where the second plurality of analytes is not coupled to the first plurality of beads. The removal may be performed using the solution.

At block 1960, an amount of the first subset of the plurality of label compounds in the second mixture may be measured. Measuring the amount of label compounds may include measuring an intensity (e.g., a fluorescence intensity, pixel intensity, or electrical current). The intensity may be a normalized intensity. The location for measurement may be at a first distance from a longitudinal axis going through the outlet of the reactor. The first distance may be in a range from 0 to 1 mm, 1 to 2 mm, 2 to 3 mm, 3 to 4 mm, 4 to 5 mm, 5 to 10 mm, or greater than 10 mm. The location for measurement may be at a second distance from the reactor. The second distance may be from 1 to 2 mm, 2 to 3 mm, 3 to 4 mm, 4 to 5 mm, 5 to 10 mm, 10 to 15 mm, 15 to 20 mm, 20 to 30 mm, 30 to 50 mm, or greater than 50 mm.

At block 1970, a reaction kinetic parameter is determined using the amount of the first subset of the plurality of label compounds. The reaction kinetic parameter may be any parameter used in a kinetic rate equation. The reaction kinetic parameter may be a concentration of the plurality of analytes. For example, the concentration may be an absolute or relative concentration in the reactor or in the sample. A relative concentration may be relative to the concentration of another analyte in the reactor or in the sample. The reaction kinetic parameter may be a rate constant characterizing a binding reaction of the affinity reagent to the analyte. The reaction kinetic parameter may be a rate constant characterizing a dissociation reaction of the affinity reagent to the analyte. In some embodiments, the rate constants may be predetermined, and the concentration may be calculated using the predetermined rate constant. The reaction kinetic parameter may be determined using 10 to 20, 20 to 30, 30 to 40, 40 to 50, or 50 to 100 beads, fewer than 200 beads.

In some embodiments, the reaction kinetic parameter may be the concentration of the plurality of analytes. The concentration may be compared to a threshold value. The threshold value may be a value of a concentration that indicates the presence of a disorder, or the threshold value may be a value of a concentration that is statistically different from the minimum concentration that indicates the presence of a disorder. For example, the threshold value may be 1, 2, or 3 standard deviations above the minimum concentration. When the analyte is troponin I, the threshold value may indicate the existence or onset of a heart attack.

If the subject from whom the sample is obtained is determined to have a disorder, the subject may be treated for the disorder. For example, an alert may be sent to a medical professional or an emergency or medical facility. If the subject is determined to have a heart attack, the subject may be treated for the heart attack, which may include administering aspirin, clot busters (thrombolytics or fibrinolytics), blood thinners (e.g., heparin), nitroglycerin, morphine, beta blockers, ACE inhibitors, and/or statins. In some embodiments, the subject may undergo surgery (e.g., coronary angioplasty and stenting, coronary artery bypass surgery).

Process 1900 may be multiplexed to analyze different analytes. The plurality of analytes may be a plurality of first analytes. The sample may include a plurality of second analytes. The first analyte may be different from the second analyte. The plurality of affinity reagents may be a plurality of first affinity reagents. Process 1900 may further include mixing a second plurality of beads with the sample to form the mixture. Each bead of the second plurality of beads may be coupled to a second affinity reagent. The second affinity reagent may be configured to bind to the second analyte. Process 1900 may include binding the plurality of second analytes to a plurality of second affinity reagents coupled to the second plurality of beads.

The first plurality of beads may be characterized by diameters in a first size range. The second plurality of beads may be characterized by diameters in a second size range. The first size range may not be the second size range. The first size range and the second size range may be non-overlapping. Beads in additional size ranges may be used. For example, beads having 3, 4, 5, 6, 7, 8, 9, or 10 size ranges may be used. Beads may be in a range from 1 to 2 µm, 2 to 3 µm, 3 to 4 µm, 4 to 5 µm, 5 to 6 µm, 6 to 7 µm, 7 to 8 µm, 8 to 9 µm, 9 to 10 µm, 10 to 11 µm, 11 to 15 µm, 15 to 20 µm, 20 to 30 µm, or greater than 30 µm.

The plurality of structures may be a first plurality of structures. Process 1900 may further include flowing a second portion of the mixture from the reactor through a third fluidic path defined by a second plurality of structures in the microfluidic chip. The second plurality of structures may include different structures than the first plurality of structures.

Process 1900 further includes coupling a third subset of the plurality of label compounds to the second plurality of beads in the reactor. Process 1900 may include removing a fourth subset of the plurality of label compounds from the second portion of the mixture to form a fourth mixture including the second plurality of beads. The removal may be performed using the solution. Process 1900 may include measuring an amount of the third subset of the plurality of label compounds in the fourth mixture.

The label compounds used may be different to analyze different types of analytes. The plurality of label compounds may be a plurality of first label compounds. The sample may further include a plurality of second label compounds. The plurality of second label compounds may be configured to bind to the second analyte. The plurality of second label compounds may be different from the plurality of first label compounds. Process 1900 may further include coupling a first subset of the plurality of second label compounds to the second plurality of beads in the reactor. The first portion of the mixture may include the second plurality of beads coupled to the first subset of the plurality of second label compounds. Process 1900 may also include removing a second subset of the plurality of second label compounds from the first portion of the mixture to form the second mixture may include the second plurality of beads. The removal may be performed using the solution. Process 1900 may include measuring an amount of the first subset of the plurality of second label compounds coupled to the second plurality of beads in the second mixture.

Labels of the label compounds may have different colors. For example, 2, 3, 4, or 5 different colors of fluorophores can be used as labels. As another example, labels including quantum dots may have 2 to 5, 5 to 10, 10 to 15, or more than 15 different colors. Multiple colors can be used for each bead size.

Process 1900 may be repeated two or more times. Process 1900 may include additional implementations, such as any single implementation or any combination of implementations described herein and/or in connection with one or more other processes described elsewhere herein.

Although FIG. 19 shows example blocks of process 1900, in some implementations, process 1900 may include additional blocks, fewer blocks, different blocks, or differently arranged blocks than those depicted in FIG. 19. Additionally, or alternatively, two or more of the blocks of process 1900 may be performed in parallel.

B. Two-Step Conjugation

Figure 20:
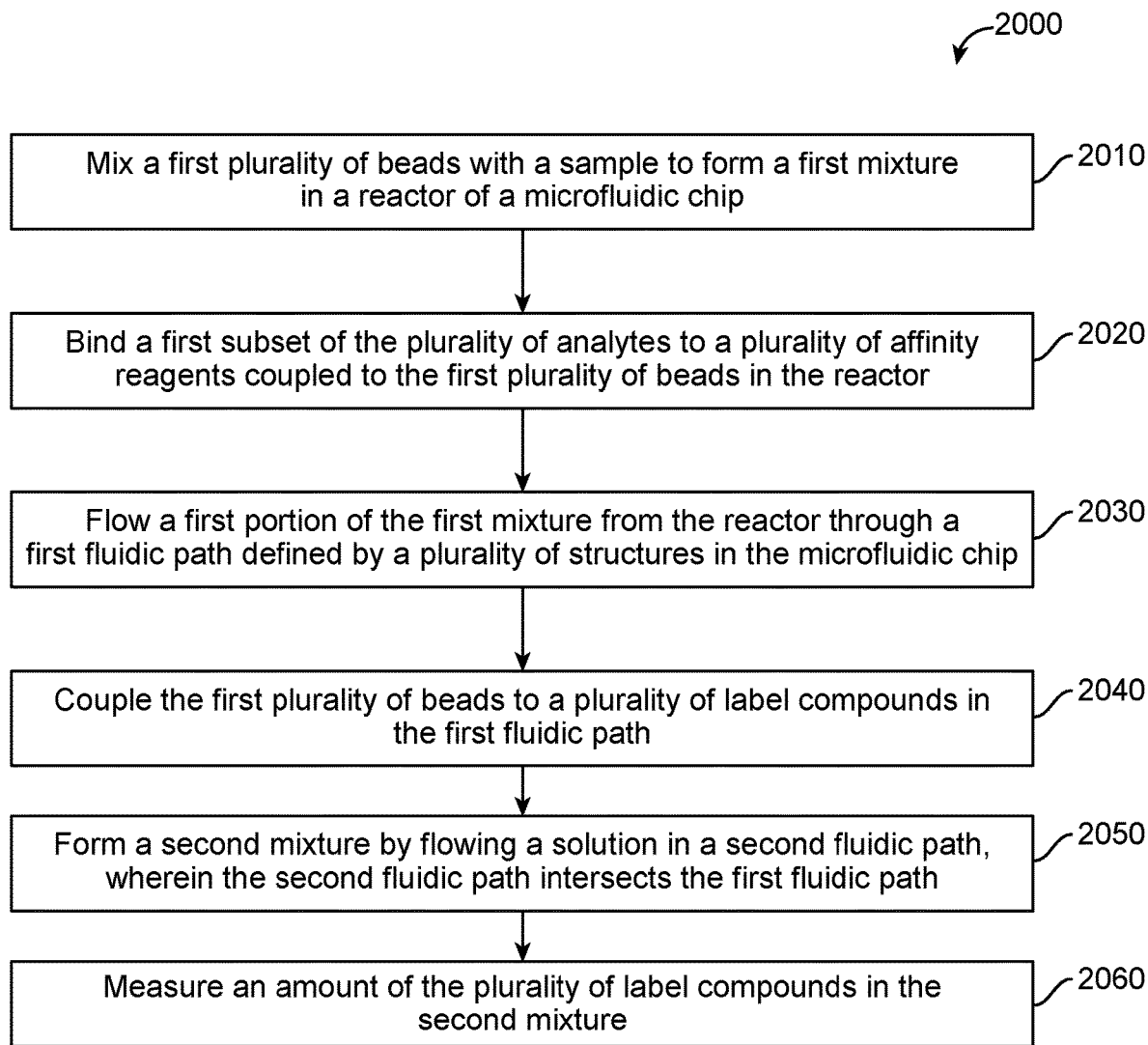
FIG. 20 is a flowchart of an example process for analyzing reaction kinetics according to embodiments of the present invention.

FIG. 20 is a flowchart of an example process 2000. Example process 2000 may be similar to example process 1900. Example process 2000 involves a two-step conjugation reaction. The reactor in process 2000 may not include label compounds. In some implementations, one or more process blocks of FIG. 20 may be performed by a system 1500 or any system described herein.

At block 2010, a first plurality of beads is mixed with a sample to form a first mixture in a reactor of a microfluidic chip. The sample may include a plurality of analytes. Each bead of the first plurality of beads may be coupled to an affinity reagent. The affinity reagent may be configured to bind to the analyte. Block 2010 may be performed in a similar manner as block 1910. However, in block 2010, the reactor may not include label compounds.

At block 2020, a first subset of the plurality of analytes is bound to a plurality of affinity reagents coupled to the first plurality of beads in the reactor. Block 2020 may be performed in a similar manner as block 1920.

At block 2030, a first portion of the first mixture is flowed from the reactor through a first fluidic path defined by a plurality of structures in the microfluidic chip. The first portion of the first mixture may include the first plurality of beads coupled to a first subset of the plurality of affinity agents. Block 2030 may be performed in a similar manner as block 1940. The first mixture may not include label compounds when it is being flowed. The first fluidic path may be fluidic path 1224 in FIG. 12.

At block 2040, the first plurality of beads is coupled to a plurality of label compounds in the first fluidic path. Block 2040 may be performed in a similar manner as block 1930. The coupling in block 2040 may not occur in the reactor. Coupling may include binding the plurality of label compounds to the first subset of the plurality of analytes. The plurality of label compounds may be flowed from a reactant reservoir to the first fluidic path. The reactant reservoir may be reactant reservoir 1228 in FIG. 12. The amount of the plurality of label compounds may be in excess of the amount of the first subset of the plurality of analytes or the plurality of analytes. For example, the amount of the plurality of label compounds may be at least 1.5, 2, 3, 4, 5, 6, 7, 8, 9, 10, 10 to 20, 20 to 50, or 50 to 100 times the amount of the first subset of the plurality of analytes or the plurality of analytes.

At block 2050, a second mixture is formed by flowing a solution in a second fluidic path. The solution may be flowed from a reservoir, including reservoir 1240 of FIG. 12. The second fluidic path may intersect the first fluidic path. Block 2050 may be performed in a similar manner as block 1950.

At block 2060, an amount of the plurality of label compounds in the second mixture is measured. Block 2060 may be performed in a similar manner as block 1960.

In some embodiments, process 2000 may further include determining a reaction kinetic parameter using the amount of the plurality of label compounds. Determining the reaction kinetic parameter may be performed in a similar manner as in block 1970.

Process 2000 may be multiplexed to analyze different analytes. The plurality of analytes may be a plurality of first analytes. The sample may include a plurality of second analytes. The first analyte is different from the second analyte. The plurality of affinity reagents may be a plurality of first affinity reagents. The process may further include mixing a second plurality of beads with the sample to form the first mixture. Each bead of the second plurality of beads may be coupled to a second affinity reagent. The second affinity reagent may be configured to bind to the second analyte and not the first analyte. The plurality of second analytes may be bound to a plurality of second affinity reagents coupled to the second plurality of beads.

The first plurality of beads may be characterized by diameters in a first size range. The second plurality of beads is characterized by diameters in a second size range. The first size range is not the second size range. The first size range and the second size range may be any of the ranges described herein, including with process 1900.

The plurality of structures may be a first plurality of structures. Process 2000 may further include flowing a second portion of the first mixture from the reactor through a third fluidic path defined by a second plurality of structures in the microfluidic chip. The second plurality of structures may include different structures than the first plurality of structures.

Process 2000 may further include coupling a second subset of the plurality of label compounds to the second plurality of beads in the third fluidic path. Process 2000 may include measuring an amount of the second subset of the plurality of label compounds. Multiplexing in process 2000 may be similar to what is described in process 1900. Coupling the second subset of the plurality of label compounds to the second plurality of beads may not occur in the reactor.

Process 2000 may further include removing a fourth subset of the plurality of label compounds from the second portion of the first mixture to form a third mixture. The third mixture may include the second plurality of beads. Measuring the amount of the second subset of the plurality of label compounds may be in the third mixture.

The plurality of label compounds may be a plurality of first label compounds. The plurality of second label compounds may be configured to bind to the second analyte. The plurality of second label compounds may be different from the plurality of first label compounds. Process 2000 may further include coupling a first subset of the plurality of second label compounds to the second plurality of beads. The coupling may be outside the reactor and in a fluidic path (e.g., third fluidic path). The first portion of the first mixture may include the second plurality of beads. Process 2000 may include removing a second subset of the plurality of second label compounds from the first subset of the plurality of second label compounds. A third mixture may include the first subset of the plurality of second label compounds. Process 2000 may include measuring an amount of the first subset of the plurality of second label compounds coupled to the second plurality of beads in the third mixture.

Process 2000 may include additional implementations, such as any single implementation or any combination of implementations described herein and/or in connection with one or more other processes described elsewhere herein.

Although FIG. 20 shows example blocks of process 2000, in some implementations, process 2000 may include additional blocks, fewer blocks, different blocks, or differently arranged blocks than those depicted in FIG. 20. Additionally, or alternatively, two or more of the blocks of process 2000 may be performed in parallel.

C. Reaction Kinetic Parameter

Figure 21:
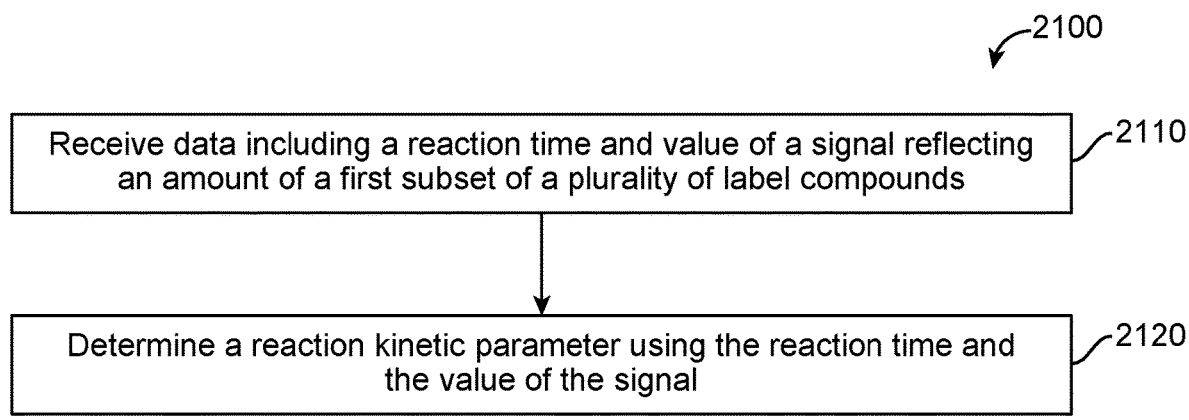
FIG. 21 is a flowchart of an example process for determining a reaction kinetic parameter according to embodiments of the present invention.

FIG. 21 is a flowchart of an example process 2100. In some implementations, one or more process blocks of FIG. 21 may be performed by a system, including system 1500, computer system 10, or any system described herein. The blocks in process 2100 may be computer-implemented.

At block 2110, data including a reaction time and value of a signal reflecting an amount of a first subset of a plurality of label compounds may be received. The value of the signal may be obtained by all or part of process 1900, process 2000, or any method described herein.

The value of the signal may not be the absolute amount of the first subset of the plurality of label compounds. The value of the signal may be measured. The signal may be a fluorescence signal. The value may be an intensity.

At block 2120, a reaction kinetic parameter may be determined using the reaction time and the value of the signal. The reaction kinetic parameter may be an amount of the affinity reagent in the sample. Determining the reaction kinetic parameter may include inputting the time and the value of the signal into an equation relating time and value of the signal to the reaction kinetic parameter. The equation may be an analytical or simplified equation, including any equation described herein. The equation may be determined empirically from one or more calibration samples having known values of the reaction kinetic parameter.

Determining the reaction kinetic parameter may include comparing the value of the signal at the time to a calibration value at the time. The calibration value may be determined from one or more calibration samples having known values of the reaction kinetic parameter at the time.

The reaction kinetic parameter may be any reaction kinetic parameter described herein. The reaction kinetic parameter may be used as described with process 1900, process 2000, or any method described herein. The reaction kinetic parameter is obtained using new types of data and new systems and techniques for acquiring the data.

Process 2100 may include additional implementations, such as any single implementation or any combination of implementations described herein and/or in connection with one or more other processes described elsewhere herein.

Although FIG. 21 shows example blocks of process 2100, in some implementations, process 2100 may include additional blocks, fewer blocks, different blocks, or differently arranged blocks than those depicted in FIG. 21. Additionally, or alternatively, two or more of the blocks of process 2100 may be performed in parallel.

V. Example Systems

Figure 22:
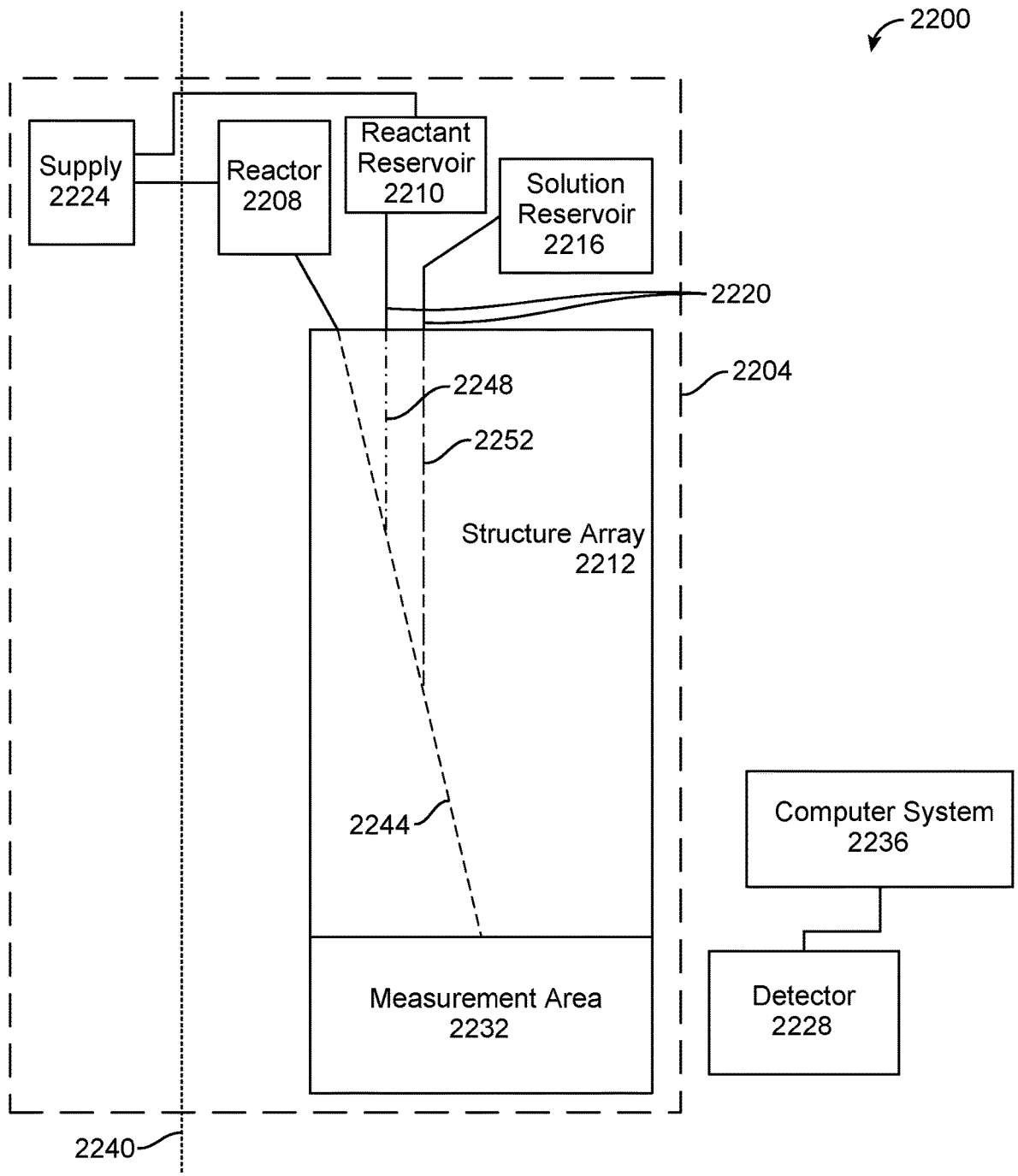
FIG. 22 shows a system for analyzing reaction kinetics according to embodiments of the present invention.

FIG. 22 shows a system 2200 for analyzing reaction kinetics. System 2200 may perform all or part of process 1900, process 2000, or process 2100. In embodiments, system 2200 may include a microfluidic chip 2204. Microfluidic chip 2204 may include a reactor 2208. Reactor 2208 may have a volume from 1 to 5 µL, 5 to 10 µL, 10 to 15 µL, 15 to 20 µL, 20 to 30 µL, or greater than 30 µL. Reactor 2208 may have a volume of 20 µL or less. Reactor 2208 may be reactor 604, reactor 710, reactor 1204, or any reactor described herein. Reactor 2208 may include an agitator (e.g., a stirrer) or a heater.

Microfluidic chip 2204 may include a structure array 2212. The structure array may be a DLD array (e.g., DLD array 712). The structure array may include a plurality of parallel rows of structures and a plurality of parallel columns of structures. Microfluidic chip 2204 may have a first longitudinal axis 2240. The array of structures may have a second longitudinal axis 2244. Second longitudinal axis 2244 may be offset from first longitudinal axis 2240. The axes may not be parallel. Second longitudinal axis 2244 and first longitudinal axis 2240 may form an angle from 10 to 20 degrees, 20 to 30 degrees, 30 to 40 degrees, 40 to 50 degrees, 50 to 60 degrees, 60 to 70 degrees, or 70 to 80 degrees. The angle formed may be an angle calculated with FIGS. 9A to 9C. For example, the angle may be equal to or within 5% or 10% of $\tan^{-1}(1/N)$, where N is an integer from 1 to 30.

Each structure of the plurality of structures may be characterized by a diameter in a range from 1 to 2 µm, 2 to 3 µm, 3 to 4 µm, 4 to 5 µm, 5 to 6 µm, 6 to 7 µm, 7 to 8 µm, 8 to 9 µm, 9 to 10 µm, 10 to 11 µm, 11 to 15 µm, 15 to 20 µm, 20 to 30 µm, or greater than 30 µm. The structures may have a height from 1 to 2 µm, 2 to 3 µm, 3 to 4 µm, 4 to 5 µm, 5 to 6 µm, 6 to 7 µm, 7 to 8 µm, 8 to 9 µm, 9 to 10 µm, 10 to 11 µm, 11 to 15 µm, 15 to 20 µm, 20 to 30 µm, or greater than 30 inn. A structure may be separate from the closest structure by a distance in a range from 1 to 2 µm, 2 to 3 µm, 3 to 4 µm, 4 to 5 µm, 5 to 6 µm, 6 to 7 µm, 7 to 8 µm, 8 to 9 µm, 9 to 10 µm, 10 to 11 µm, 11 to 15 µm, 15 to 20 µm, 20 to 30 µm, or greater than 30 µm. The height of the structures may be equal or about equal (e.g., within 5%, 10%, or 20%) of the distance separating a structure from the closest structure. The diameter of the pillars may be equal or about equal to the height of the structures. The diameter of the beads may be calculated by the equation $$\frac{Dc}{G} \cong \alpha \times \epsilon^\beta,$$

as explained above. The diameter of the beads may be a function of the distance between adjacent structures and the number of structures for a shift on structure to the right.

The structures may not be or include electrodes connected to a power source or magnets. In embodiments, microfluidic chip 2204 may also not include electrodes or magnets.

Structure array 2212 may include a plurality of structures defining a first fluidic path, which may be parallel or substantially parallel to second longitudinal axis 2244. The first fluidic path may be path 716 in FIG. 7A. The first fluidic path may be in fluid communication with reactor 2208, a reactant reservoir 2210, and a solution reservoir 2216.

Reactant reservoir 2210 may be reactant reservoir 1228 or any reactant reservoir described herein. A manifold 2220 may be configured to deliver a reactant from the reactant reservoir to intersect the first fluidic path. The manifold may deliver the solution in a direction parallel to first longitudinal axis 2240. For example, the path of the reactant may be path 2248. A plurality of label compounds may be disposed in reactant reservoir 2210. The reactant may be the label compound.

Manifold 2220 may be configured to deliver a solution from solution reservoir 2216 to intersect the first fluidic path. The solution may be a buffer solution to clean the beads. Solution reservoir 2216 may be buffer reservoir 1420. The manifold may deliver the solution in a direction parallel to first longitudinal axis 2240. For example, the path of the solution may be path 2252 or path 724 in FIG. 7A.

In some embodiments, the plurality of structures may include different sections of structures. In embodiments, each section of the structures may have a different longitudinal axis than an adjacent section. In some embodiments, each section of the structures may have different gap distances, diameters, and/or heights than an adjacent section.

System 2200 may in addition include a plurality of beads disposed on microfluidic chip 2204. The plurality of beads may be disposed in supply 2224. Supply 2224 may be a holding area for beads, analytes, and/or label compounds before they are introduced into reactor 2208 or reactant reservoir 2210. Each bead of the plurality of beads may have a diameter smaller than a width of the first fluidic path. Each bead of the plurality of beads may be bound to a first affinity reagent. The beads may be any beads described herein, including bead 608, bead 750, bead 766, bead 804, bead 1012, microsphere 1116, bead of ligand-microsphere complex 1212, bead 1404, bead 1408, or bead 1412. The first affinity reagent may be an antibody or an oligonucleotide. For example, the first affinity reagent may be antibody 610 or any antibody described herein.

System 2200 may include a plurality of label compounds. The label compounds may not be coupled to the plurality of beads. The label compounds may be disposed in reactor 2208 and/or reactant reservoir 2210. Each label compound may include a second affinity reagent. Each second affinity reagent may be bound to a label. The second affinity reagent may be the antibody portion of labeled sandwich antibody 616. The second affinity reagent may be any antibody described herein. The label may be a fluorophore, quantum dot, chemiluminescent tag, electrochemical tag, or any label described herein.

System 2200 may include a plurality of analytes. The analytes may be any antigen described herein, including a protein. The plurality of first affinity reagents may be configured to bid to the analytes. The plurality of second affinity reagents may be configured to bind to the plurality of analytes.

The analytes, affinity reagents, label compounds, and/or beads may be located in supply 2224 or reactor 2208.

System 2200 may also include a detector 2228. Detector 2228 may be an imaging detector (e.g., a camera). Detector 2228 may be positioned to detect and/or measure a signal in measurement area 2232. Measurement area 2232 may be a portion of structure array 2212. Detector 2228 may be configured to detect the label. In some embodiments, detector 2228 may be part of or contacting microfluidic chip 2204. Detector 2228 may be controlled by computer system 2236. Computer system 2236 may receive data from detector 2228. Data may indicate the intensity of the signal and/or a time when the signal was measured.

VI. Computer System

Figure 23:
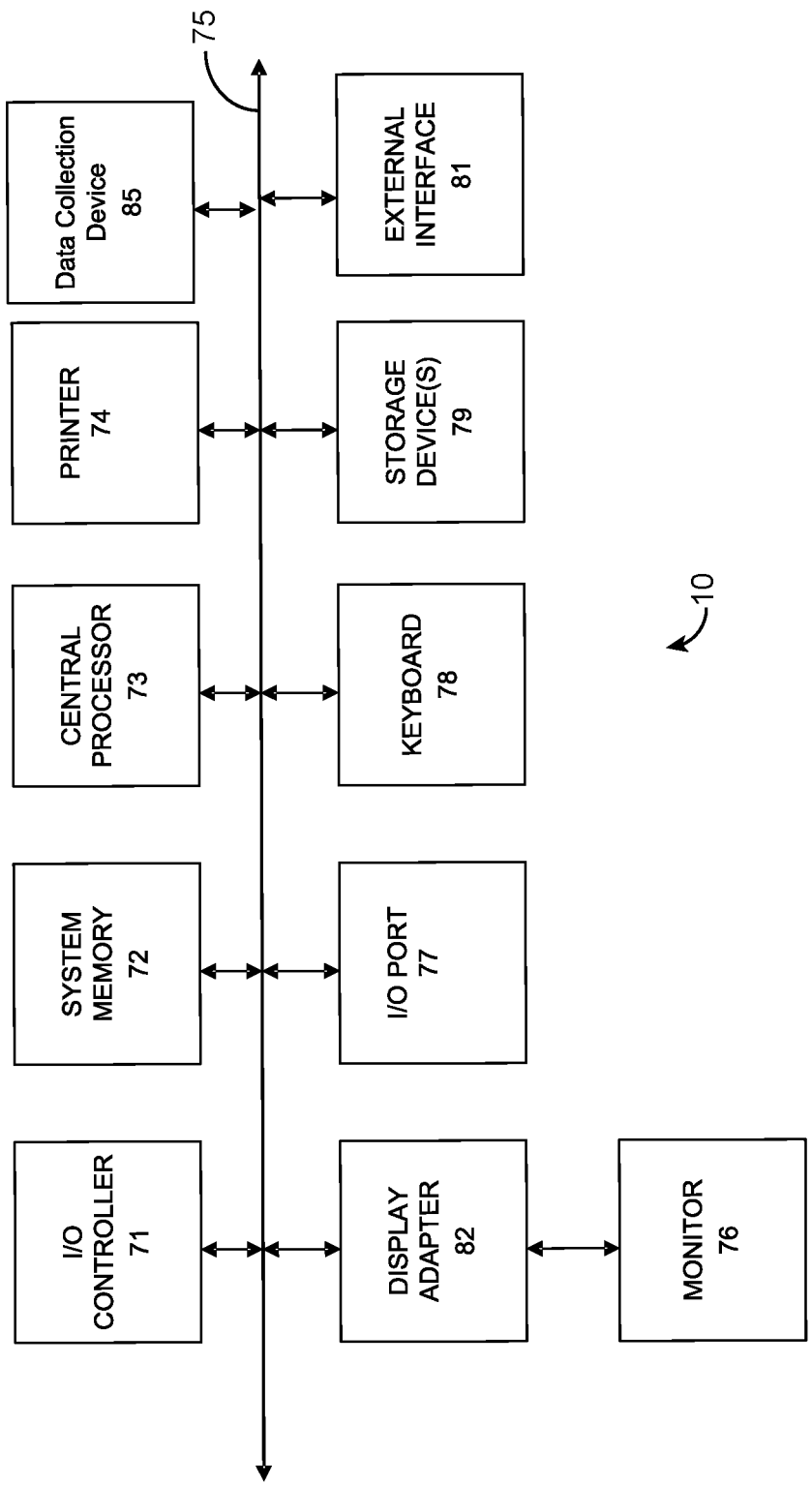
FIG. 23 shows a computer system according to embodiments of the present invention.

Any of the computer systems mentioned herein may utilize any suitable number of subsystems. Examples of such subsystems are shown in FIG. 23 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices. Computer system 10 may be computer system 2236.

The subsystems shown in FIG. 23 are interconnected via a system bus 75. Additional subsystems such as a printer 74, keyboard 78, storage device(s) 79, monitor 76 (e.g., a display screen, such as an LED), which is coupled to display adapter 82, and others are shown. Peripherals and input/output (I/O) devices, which couple to I/O controller 71, can be connected to the computer system by any number of means known in the art such as input/output (I/O) port 77 (e.g., USB, Lightning). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g., an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present disclosure using hardware and a combination of hardware and software.

Any of the software components or functions described in this application may be implemented as software code to be executed by a processor using any suitable computer language such as, for example, Java, C, C++, C #, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive, or an optical medium such as a compact disk (CD) or DVD (digital versatile disk) or Blu-ray disk, flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g., a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order that is logically possible. Additionally, portions of these steps may be used with portions of other steps from other methods. Also, all or portions of a step may be optional. Additionally, any of the steps of any of the methods can be performed with modules, units, circuits, or other means of a system for performing these steps.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The above description of example embodiments of the present disclosure has been presented for the purposes of illustration and description and are set forth so as to provide those of ordinary skill in the art with a complete disclosure and description of how to make and use embodiments of the present disclosure. It is not intended to be exhaustive or to limit the disclosure to the precise form described nor are they intended to represent that the experiments are all or the only experiments performed. Although the disclosure has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the disclosure being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

The claims may be drafted to exclude any element which may be optional. As such, this statement is intended to serve as antecedent basis for use of such exclusive terminology as "solely", "only", and the like in connection with the recitation of claim elements, or the use of a "negative" limitation.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within embodiments of the present disclosure. The upper and lower limits of these smaller ranges may independently be included or excluded in the range, and each range where either, neither, or both limits are included in the smaller ranges is also encompassed within the present disclosure, subject to any specifically excluded limit in the stated range. Where the stated range includes one or both of the limits, ranges excluding either or both of those included limits are also included in the present disclosure.

All patents, patent applications, publications, and descriptions mentioned herein are hereby incorporated by reference in their entirety for all purposes as if each individual publication or patent were specifically and individually indicated to be incorporated by reference and are incorporated herein by reference to disclose and describe the methods and/or materials in connection with which the publications are cited. None is admitted to be prior art.

What is claimed is:

1. A method for analyzing reaction kinetics of a binding reaction, the method comprising:
    mixing a first plurality of beads with a sample to form a first mixture in a reactor of a microfluidic chip, wherein:
        the sample comprises a plurality of analytes,
        each bead of the first plurality of beads is coupled to an affinity reagent, and
        the affinity reagent is configured to bind to the analyte;
    binding a first subset of the plurality of analytes to a plurality of affinity reagents coupled to the first plurality of beads in the reactor;
    flowing a first portion of the first mixture from the reactor through a first fluidic path defined by a plurality of structures in the microfluidic chip, wherein:
        the first portion of the first mixture comprises the first plurality of beads coupled to a first subset of the plurality of affinity reagents,
        the plurality of structures comprises a plurality of pillars,
        the plurality of pillars is a portion of an array of pillars, and
        the array of pillars is characterized by a plurality of rows and a plurality of columns;
    coupling the first plurality of beads to a plurality of label compounds in the first fluidic path;
    flowing a solution in a second fluidic path, wherein the second fluidic path intersects the first fluidic path; and
    measuring an amount of the plurality of label compounds coupled to the first plurality of beads.

2. The method of claim 1, further comprising:
    removing a second subset of the plurality of analytes from the first portion of the first mixture before coupling the first plurality of beads to the plurality of label compounds in the first fluidic path.

3. The method of claim 1, wherein the plurality of label compounds is a first plurality of label compounds,
    the method further comprising:
        flowing the first plurality of label compounds and a second plurality of label compounds in a third fluidic path, wherein the third fluidic path intersects the first fluidic path, and
        removing the second plurality of label compounds from the first fluidic path.

4. The method of claim 1, wherein:
    the analyte is an antigen,
    the affinity reagent is an antibody, and
    each label of the plurality of label compounds comprises a fluorescent label.

5. The method of claim 1, wherein:
    the plurality of pillars comprises pillars from at least five columns from the plurality of columns.

6. The method of claim 1, wherein:
    the microfluidic chip has a longitudinal axis, and
    the first fluidic path and the longitudinal axis form an angle in a range from 10 degrees to 60 degrees.

7. The method of claim 1, wherein:
    the microfluidic chip has a longitudinal axis, and
    the second fluidic path is parallel to the longitudinal axis.

8. The method of claim 1, wherein:
    the plurality of analytes is a first plurality of analytes,
    the method further comprising:
        removing, using the solution, a second plurality of analytes, wherein the second plurality of analytes is not coupled to the first plurality of beads.

9. The method of claim 1, wherein measuring the amount of label compounds comprises measuring a fluorescence.

10. The method of claim 1, further comprising:
    determining a reaction kinetic parameter using the amount of the plurality of label compounds.

11. The method of claim 10, wherein the reaction kinetic parameter is a concentration of the plurality of analytes.

12. The method of claim 11, wherein determining the reaction kinetic parameters comprises determining the concentration of the plurality of analytes is in a range from 1 pM to 500 pM.

13. The method of claim 10, wherein the reaction kinetic parameter is a rate constant characterizing the binding reaction of the affinity reagent to the analyte.

14. The method of claim 1, wherein:
the plurality of analytes is a plurality of first analytes,
the sample comprises a plurality of second analytes,
the first analyte is different from the second analyte, and
the plurality of affinity reagents is a plurality of first affinity reagents,
the method further comprising:
mixing a second plurality of beads with the sample to form the first mixture, wherein:
  each bead of the second plurality of beads is coupled to a second affinity reagent, and
  the second affinity reagent is configured to bind to the second analyte, and
binding the plurality of second analytes to a plurality of second affinity reagents coupled to the second plurality of beads.

15. The method of claim 14, wherein:
the first plurality of beads is characterized by diameters in a first size range,
the second plurality of beads is characterized by diameters in a second size range, and
the first size range is not the second size range.

16. The method of claim 15, wherein:
the plurality of structures is a first plurality of structures,
the method further comprising:
flowing a second portion of the first mixture from the reactor through a third fluidic path defined by a second plurality of structures in the microfluidic chip, wherein the second plurality of structures comprises different structures than the first plurality of structures.

17. The method of claim 16, further comprising:
coupling a second subset of the plurality of label compounds to the second plurality of beads in the third fluidic path, and
measuring an amount of the second subset of the plurality of label compounds.

18. The method of claim 17, further comprising:
removing a fourth subset of the plurality of label compounds from the second portion of the first mixture to form a third mixture comprising the second plurality of beads,
wherein measuring the amount of the second subset of the plurality of label compounds is in the third mixture.

19. The method of claim 14, wherein:
the plurality of label compounds is a plurality of first label compounds,
a plurality of second label compounds is configured to bind to the second analyte, and
the plurality of second label compounds is different from the plurality of first label compounds,
the method further comprising:
coupling a first subset of the plurality of second label compounds to the second plurality of beads, and
measuring an amount of the first subset of the plurality of second label compounds coupled to the second plurality of beads.

20. The method of claim 1, wherein:
the analyte is a nucleic acid molecule, and
the affinity reagent is an oligonucleotide comprising a sequence of nucleotides complementary to a portion of the nucleic acid molecule.

21. The method of claim 1, wherein the first mixture in the reactor has a volume from 1 to 30 µL.

22. The method of claim 1, further comprising flowing the plurality of label compounds from a reservoir to the first fluidic path.

23. The method of claim 22, wherein:
the microfluidic chip has a longitudinal axis, and
flowing the plurality of label compounds comprises flowing the plurality of label compounds parallel to the longitudinal axis.

24. The method of claim 1, further comprising:
forming a second mixture from the intersection of the solution in the second fluidic path with the first plurality of beads in the first fluidic path,
wherein measuring the amount of the plurality of label compounds is in the second mixture.

* * * * *